US010383912B2

(12) United States Patent
Berkman et al.

(10) Patent No.: US 10,383,912 B2
(45) Date of Patent: Aug. 20, 2019

(54) TUNABLE PH-SENSITIVE LINKER FOR CONTROLLED DRUG RELEASE

(71) Applicant: Washington State University, Pullman, WA (US)

(72) Inventors: Clifford E. Berkman, Pullman, WA (US); Corinne Ley, Pullman, WA (US); Jonathan Geruntho, Pullman, WA (US); Cindy Choy, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 15/504,990

(22) PCT Filed: Aug. 17, 2015

(86) PCT No.: PCT/US2015/045550
§ 371 (c)(1),
(2) Date: Feb. 17, 2017

(87) PCT Pub. No.: WO2016/028700
PCT Pub. Date: Feb. 25, 2016

(65) Prior Publication Data
US 2017/0258936 A1    Sep. 14, 2017

Related U.S. Application Data

(60) Provisional application No. 62/151,293, filed on Apr. 22, 2015, provisional application No. 62/038,692, filed on Aug. 18, 2014.

(51) Int. Cl.
*A61K 38/06*   (2006.01)
*A61K 51/10*   (2006.01)
*A61K 47/68*   (2017.01)

(52) U.S. Cl.
CPC .......... *A61K 38/06* (2013.01); *A61K 47/6803* (2017.08); *A61K 47/6869* (2017.08); *A61K 47/6889* (2017.08); *A61K 51/1072* (2013.01)

(58) Field of Classification Search
CPC ......... A61K 38/06; A61K 47/68; A61K 51/00
See application file for complete search history.

(56) References Cited

U.S. PATENT DOCUMENTS

| 2004/0161405 | A9* | 8/2004 | Rothbard | ............... | A61K 47/54 |
| | | | | | 424/78.22 |
| 2010/0183517 | A1* | 7/2010 | Berkman | ............... | C07F 9/091 |
| | | | | | 424/9.1 |

OTHER PUBLICATIONS

Du et al. Tailor-Made Dual pH-Sensitive Polymer-Doxorubicin Nanoparticles for Efficient Anticancer Drug Delivery, JACS, 133, 17560-17563. (Year: 2011).*
Du et al., "Tailor-Made Dual pH-Sensitive Polymer—Doxorubicin Nanoparticles for Efficient Anticancer Drug Delivery", Journal of American Chemical Society, 2011, vol. 133, pp. 17560-17563.
PCT Search Report and Written Opinion dated Nov. 27, 2015 for PCT Application No. PCT/US15/45550, 8 pages.

* cited by examiner

*Primary Examiner* — Michael G. Hartley
*Assistant Examiner* — Jagadishwar R Samala
(74) *Attorney, Agent, or Firm* — Lee & Hayes, P.C.

(57) ABSTRACT

A novel acid labile linker for targeted delivery and/or controlled release of agents is introduced herein. There is further disclosed a method of developing a therapeutic or diagnostic conjugate for targeted cell-specific delivery. More specifically, the invention is focused on linkers used to deliver anticancer agents to specific tumor cells.

29 Claims, 12 Drawing Sheets

*phosphoryl hydroxypropylglycine*
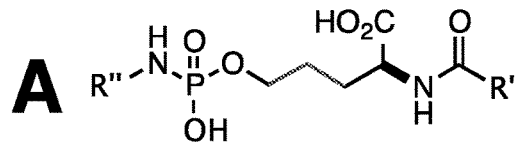
*unstable below pH 3*
*phosphoryl homoserine*
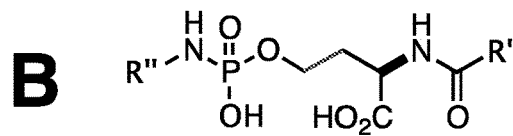
*unstable below pH 4.5*
*phosphoryl serine*
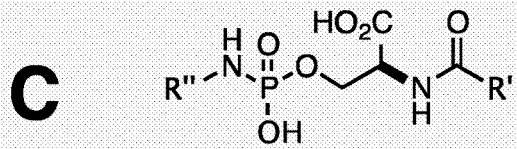
*unstable below pH 6.5*
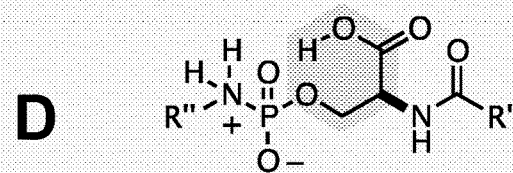
↓ hydrolysis
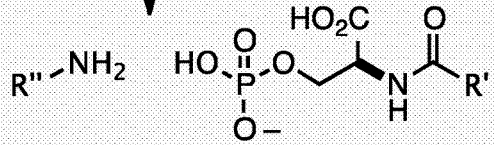
Figure 1

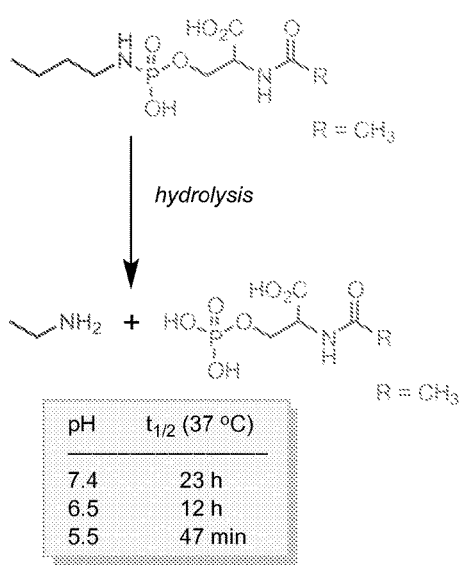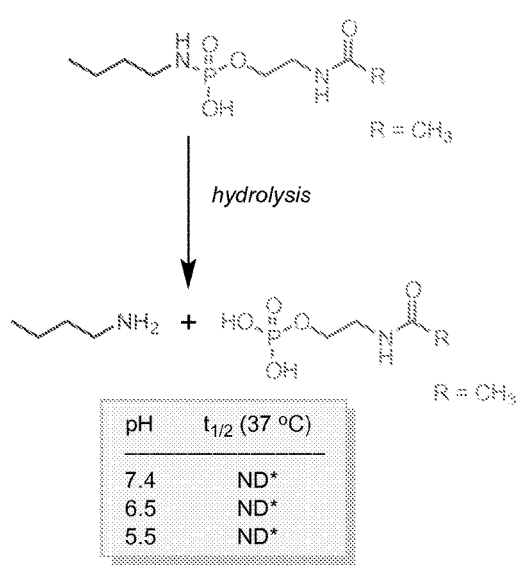
Figure 3A  Figure 3B

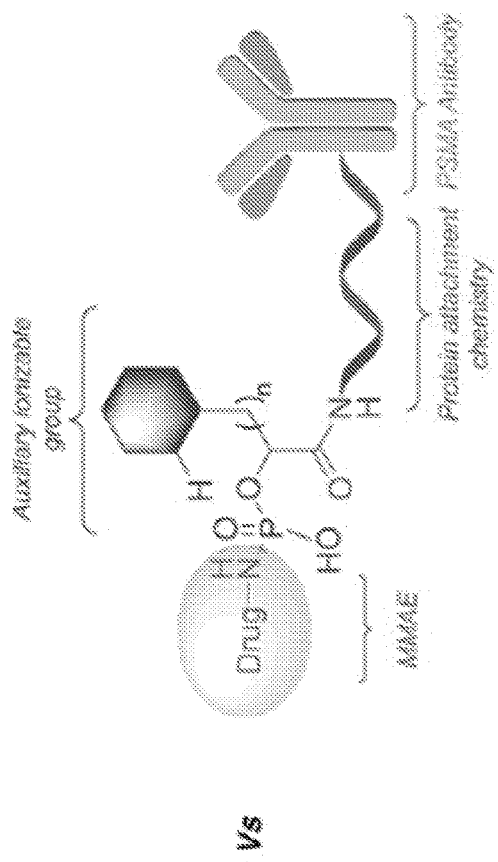
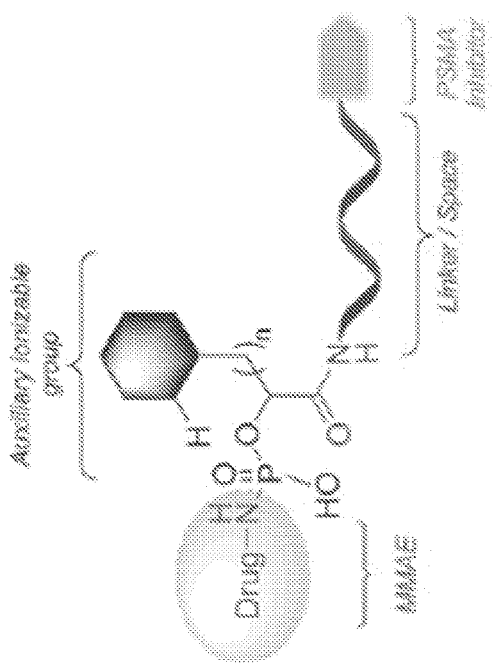
Figure 12

TUNABLE PH-SENSITIVE LINKER FOR CONTROLLED DRUG RELEASE

CROSS REFERENCE TO RELATED APPLICATION

The present claims the benefit of an earlier filing date of U.S. Provisional Patent Application No. 62/038,692 filed Aug. 18, 2014, and U.S. Provisional Patent Application No. 62/151,293 filed Apr. 22, 2015, both of which are incorporated by reference herein in their entirety.

GOVERNMENT SUPPORT

This invention was made with government support under grant no. R01 CA140617 awarded by the National Institutes of Health. The government has certain rights in the invention.

FIELD

The present disclosure provides conjugates that comprise a tunable pH sensitive functional group that triggers the release of an attached agent from the functional group itself or from a targeting molecule or other chemical or biochemical structure in which the agent is attached through this functional group. More specifically, the disclosure disclosed herein relate to a prodrug functional group or a linker, which is more stable at physiological pH than at an acidic pH and as a result rapidly releases a drug from the prodrug conjugate or from a targeting drug conjugate at acidic pH.

BACKGROUND

Controlled chemical release is a desirable characteristic in a number of applications: e.g., prodrug therapy, targeted drug conjugates, or chemical probes of chemical, biochemical, and biological environments. A topic in controlled chemical release that has been the focus of significant research efforts is chemical release of a molecule from a larger entity under different pH conditions. In many applications, it is desirable for a chemical structure to allow little or no chemical release at physiological pH and above, but have the rate of chemical release occur significantly faster at lower pH. Ideal characteristics of such a chemical structure would be that the rate of chemical release could be tuned to desired rates of release at various pH conditions that could be tailored for the structure of the entity being released. The most notable applications requiring such technology is the field of antibody-drug conjugates and drug eluting stents, but it is envisaged that the technology could be applied to prodrug design, intracellular probes, and degradable polymers.

Despite extensive research, most anticancer drugs have nonspecific toxicity and do not explicitly discriminate between healthy and tumor cells. Therefore, they only gain a limited selectivity for malignant cells. Narrow therapeutic windows limit the efficacy of such drugs and result in severe side effects. Due to lack of selectivity, high concentrations of a drug that is required to eradicate the tumor are often not used. In addition, tumors can develop resistance against anticancer drugs after prolonged treatment. Therefore, achieving improved tumor selectivity through targeting of cytotoxic drugs to the cancer cells is needed.

Attaching the cytotoxic drug to a tumor-recognizing ligand (e.g., an antibody, a low molecular weight ligand or cell-specific inhibitor molecules) is considered as one of the promising approaches for tumor specific drug delivery. However, major drawbacks of such attachments are that they can potentially introduce steric hindrances and prevent association of the drug with its molecular target. Therefore, to improve the therapeutic efficacy, the active agent is frequently linked to its targeting ligand through a cleavable spacer that is stable in circulation but readily hydrolyzed or designed to be enzymatically cleaved upon entry into the target cell.

Linkers that are selectively hydrolyzed or decomposed at acidic pH have received considerable attention because the majority of receptor-directed drugs are delivered to endosomal compartments or lysosomes where pH values are thought to be low (Kratz et al., Drug polymer conjugates containing acid-cleavable bonds *Crit Rev Ther Drug Carrier Syst* 16, 245-288 (1999)). The slightly acidic microenvironment of some tumors (~pH 6.5) has also been proposed to assist in release of these drugs, especially when the conjugate is expected to be trapped within the tumor for prolonged periods (Gatenby et al., 2006 Acid-mediated tumor invasion: a multidisciplinary study. *Cancer Res* 66: 5216-5223 (2006)).

Several acid labile linkers have been reported for conjugations of certain classes of small molecules, cytotoxic agents and antibodies. In-depth description of these linkers are available in patent application US 2011/0053878A1, entitled "Acid-labile linkers for drug delivery" by Yang et al; patent application PCT/EP2013/000513, entitled 'Combinations of albumin-based drug delivery system by Kratz et al. Several other research publications also describe such linkers, for example by Etrych et al. entitled 'New HPMA copolymers containing doxorubicin bound via pH sensitive linkage: synthesis and preliminary in vitro and in vivo biological properties', published in the *Journal of Controlled Release* 73: 89-102 (2002); and by Greenfield et al. entitled 'Evaluation in vitro of andriamycin immune conjugates synthesized using an acid labile hydrazone linker', published in *Cancer Research Journal* 50: 6600-6607 (1997).

Current pH-sensitive linkers suffer from the following shortcomings: 1) slow release of conjugated drugs or molecules at endosomal pH (~5.5), 2) less than ideal difference in linker stability at pH 5.5 compared to pH 7.4, and 3) limited chemical functional groups allowed for coupling to the linkers thus restricting the scope of cytotoxic drugs to be delivered. The predominate acid-labile linker is the hydrazone, while a possible emerging linker is based on an imidazole scaffold. The common hydrazone linkers are limited to a ketone or aldehyde functionality on the molecular payloads or cytotoxic drugs (e.g., doxorubicin) and the half-lives for the release of drugs range from 2-3 days under acidic conditions (e.g., pH 5.5).

While imidazole linkers allow for tunability and have significantly shorter half-lives for the release of drugs at acidic pH, they also exhibit undesirable release of drug under physiological conditions, which would lead to premature systemic drug release and potentially untoward side effects. The chemical functionalities required on the drugs for coupling to the imidazole linkers appears to be limited to aldehydes or aldehyde-containing spacers.

Although several acid labile linkers are available, there is no such linker which is tunable, can be applied for delivery of a broad range of drugs, and can perform uniformly for different cancer types. Thus, to date the common assumption is that no general linker design exists for all drugs conjugate systems or cancer types. Despite significant progress, each particular cancer types must be examined separately in order to optimize a specific linker based drug delivery system.

Therefore, researchers are looking for pH sensitive linkers which can be enabled for attachment to a wide range of cytotoxic agents, which the stability of the linker can be adjusted for release under broad range of pH conditions, and which can be enabled to rapidly release conjugated therapeutic agents at the target site. These then will provide a means to rapidly synthesize a range of targeted cell-specific drug conjugates that can be released at a controlled rate in a targeted cell-specific environment. Such acid-labile linkers can further be used as part of a delivery mode for compounds other than therapeutic agents, such as, for example, bio-imaging agents. In addition, such linkers can be used for the controlled release of other therapeutic molecules, drugs, or other chemical and biochemical structures from a wide range of matrices and polymers.

SUMMARY

The present application is directed to pH-sensitive molecules and chemical moieties or substructures, the hydrolysis of which can be tuned for different pH conditions, and to methods of use thereof. The pH-sensitive molecules, chemical motifs, and substructures presented herein can be used, for example, in antibody-drug conjugates, drug eluting stents, prodrugs, intracellular probes, and degradable polymers. Such systems can comprise a linker having a pH-sensitive chemical moiety, a drug, and optionally a cell-specific targeting molecule or chemical or biochemical platform. The system may also contain a non-cytotoxic compound, such as, for example a bio-imaging agent or detectable group (e.g., a fluorophore, a component of a FRET pair, or radioisotope).

An aspect of the present application is directed to the method of developing a drug delivery system comprising a linker with a chemical moiety, which can decompose in acidic environment or other desired conditions to release a drug. Such linkers when attached to a therapeutic agent can utilize the lower intracellular pH (for example, pH 5.5) or extracellular pH (for example, pH 6.5) of target cell types, compared to that of blood or normal tissues, to trigger the controlled release of therapeutic agents. The drug delivery system might be an antibody or a small molecule ligand or inhibitor.

Another aspect of the present application is directed to a pH-sensitive molecule or chemical functional group, attached to an agent or which can be used to link a wide range of drugs to cell-specific targeting molecules. The agent can be a therapeutic agent that has an amine containing group or an alcohol group. Cell-specific targeting molecules might be an antibody or any small molecule such as, for example, a small molecule ligand or inhibitor of a biomolecule that binds to a molecule on the cell.

In embodiments, the present disclosure provides a conjugate or a salt thereof having formula (I)

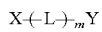  formula (I), wherein,
X is an agent comprising a moiety for attaching to L or directly to Y,
L is a spacer comprising a moiety for attaching to Y;
m is 0 or 1;
when m is 0,
X comprises a moiety $NR_1$, S, or O for attaching to Y; and
$R_1$ is H, acyl, formyl, aryl, heteroaryl, heterocycloalkyl, substituted or unsubstituted alkyl, substituted or unsubstituted cycloalkyl, substituted or unsubstituted aryl, substituted or unsubstituted heteroaryl, substituted or unsubstituted alkyl-aryl, substituted or unsubstituted cycloalkyl-aryl, substituted or unsubstituted alkyl-heteroaryl, or substituted or unsubstituted cycloalkyl-heteroaryl;

when m is 1,
X comprises $NR_1$, S or O for attaching to L;
L comprises a moiety $NR_1$, S, or O for attaching to Y; and
$R_1$ is H, acyl, formyl, aryl, heteroaryl, heterocycloalkyl, substituted or unsubstituted alkyl, substituted or unsubstituted cycloalkyl, substituted or unsubstituted aryl, substituted or unsubstituted heteroaryl, substituted or unsubstituted alkyl-aryl, substituted or unsubstituted cycloalkyl-aryl, substituted or unsubstituted alkyl-heteroaryl, or substituted or unsubstituted cycloalkyl-heteroaryl;
Y is a hydrolysable linker having formula (II) or formula (III);

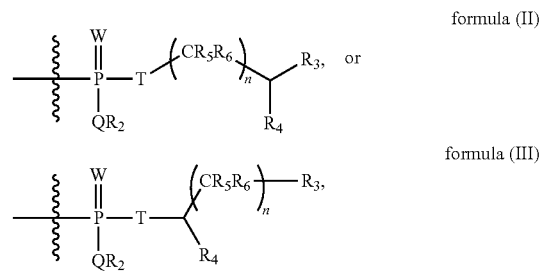

wherein,
W is O, S, or Se;
Q is N, O, S, or Se;
$R_2$ is H, substituted or unsubstituted alkyl, substituted or unsubstituted cycloalkyl, substituted or unsubstituted aryl, substituted or unsubstituted heteroaryl, substituted or unsubstituted alkyl-aryl, substituted or unsubstituted cycloalkyl-aryl, substituted or unsubstituted alkyl-heteroaryl, or substituted or unsubstituted cycloalkyl-heteroaryl;
$R_3$ is an ionizable group;
$R_4$ is H, lower alkyl, aryl, or a substituent comprising a functional group for attachment to a molecule;
$R_5$ and $R_6$ are independently, H, lower alkyl, or aryl;
T is O, S, NH, alkylene, arylene, acyl, formyl, or substituted or unsubstituted alylarylene; and
n is 0, 1, 2, 3, 4, 5, 6, 7, 8, or 9.

$R_3$ is an ionizable group such as a carboxylic acid. $R_3$ can further comprise a functional group for attaching a molecule such as a detectable label, targeting molecule, or a spacer.

X is a therapeutic agent or a diagnostic agent. X comprises a $NR_1$, S, or O for attaching to Y directly or through a spacer, L. In an embodiment, X comprises $NR_1$, S, or O for attaching to the spacer. In another embodiment, X comprises any functional group for attaching to L.

The therapeutic agent can be a chemotherapeutic agent comprising an amine group, such as monomethylauristatin E (MMAE), monomethylauristatin F (MMAF), or doxorubicin, for treating cancer. The diagnostic agent is an imaging agent for diagnosing a disease.

L is a spacer and comprises a moiety for attaching to Y. The moiety can be a $NR_1$ group or can comprise a sulfur atom, or an oxygen atom. The spacer can be of variable length. The spacer can comprise or can be a self-immolating spacer.

$R_4$ can be a substituent comprising a chemical or biorthogonal functional group for covalent attachment to a molecule. As an example, the substituent can comprise an azide or a maleimide for attachment to a targeting molecule or a solid support.

The conjugate or a salt thereof provided herein can further comprise a molecule, such as a targeting molecule or a detectable label, attached through the substituent of $R_4$ or through a functional group attached to the hydrolysable linker.

Provided herein are also compositions comprising a conjugate or a salt thereof disclosed herein and a carrier. The compositions can be a pharmaceutical composition comprising a conjugate disclosed herein or a salt thereof X and a pharmaceutically acceptable carrier. The conjugate can further comprise a molecule, such as a targeting molecule, a polymer, or a solid support.

The present disclosure provides a method of delivering a therapeutic agent to a subject, wherein the method comprises administering a therapeutically effective amount of a conjugate disclosed herein or a salt thereof comprising a therapeutic agent to a subject in need of such therapeutic agent. The conjugate or salt thereof can further comprise a targeting molecule.

The present disclosure also provides a method of delivering a diagnostic agent to a subject, wherein the method comprises administering an effective amount of a conjugate disclosed herein or a salt thereof comprising a diagnostic agent to a subject in need thereof and detecting the agent. The conjugate or salt thereof can further comprise a targeting molecule.

The present disclosure provides a method of treating cancer, wherein the method comprises administering a therapeutically effective amount of a conjugate disclosed herein or a salt thereof comprising a therapeutic agent to a subject in need of such treatment. The conjugate or salt thereof can further comprise a targeting molecule.

The present disclosure also provides a method of diagnosing cancer, wherein the method comprises (a) administering an effective amount of a conjugate disclosed herein or a salt thereof comprising a diagnostic agent to a subject in need of such diagnosis, and (b) detecting the diagnostic agent. The conjugate or salt thereof can further comprise a targeting molecule.

The methods provided herein can be used to treat or to diagnose prostate cancer, in which case the conjugate comprises a targeting molecule that targets the prostate specific membrane antigen on the tumor.

Provided herein are methods of obtaining a conjugate comprising an agent that can be released from the conjugate at a pH of less than 7.4. The method comprises (a) obtaining a conjugate disclosed herein or a salt thereof; (b) placing the conjugate or a salt thereof in an environment in which the pH is less than 7.4; and (c) detecting the release of the agent. The pH is between 2.5 and 7.4.

Also, provided are methods of determining the pH at which a conjugate disclosed herein or a salt thereof undergoes hydrolysis to release the attached agent. The method comprises placing a conjugate disclosed herein or a salt thereof in an environment in which the pH is 7.4 and then lowering the pH to determine when the attached agent is released from the conjugate.

BRIEF DESCRIPTION OF THE DRAWINGS

FIGS. 1A-1D show the stability at 25° C. of (A) phosphoryl hydroxypropylglycine, (B) phosphoryl homoserine, (C) phosphoryl serine, and (D) an example of a novel pH-sensitive linker.

FIGS. 3A-3B shows results for pH stability studies of an exemplary linker. The linker shown in (B) is missing the alpha-carboxylic acid from the serine scaffold and is stable under the same conditions as the exemplary linker of (A).

FIG. 12 shows examples of drug conjugates for PSMA targeted therapy: PSMA inhibitor v. PSMA antibody.

DETAILED DESCRIPTION

Figure 2:
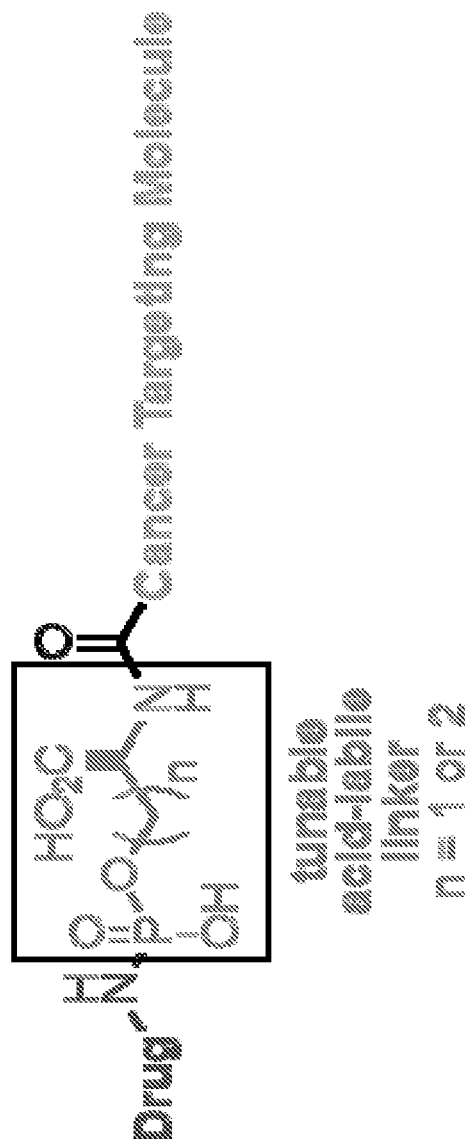
FIG. 2 shows a pH-triggered drug conjugate.
Figure 4:
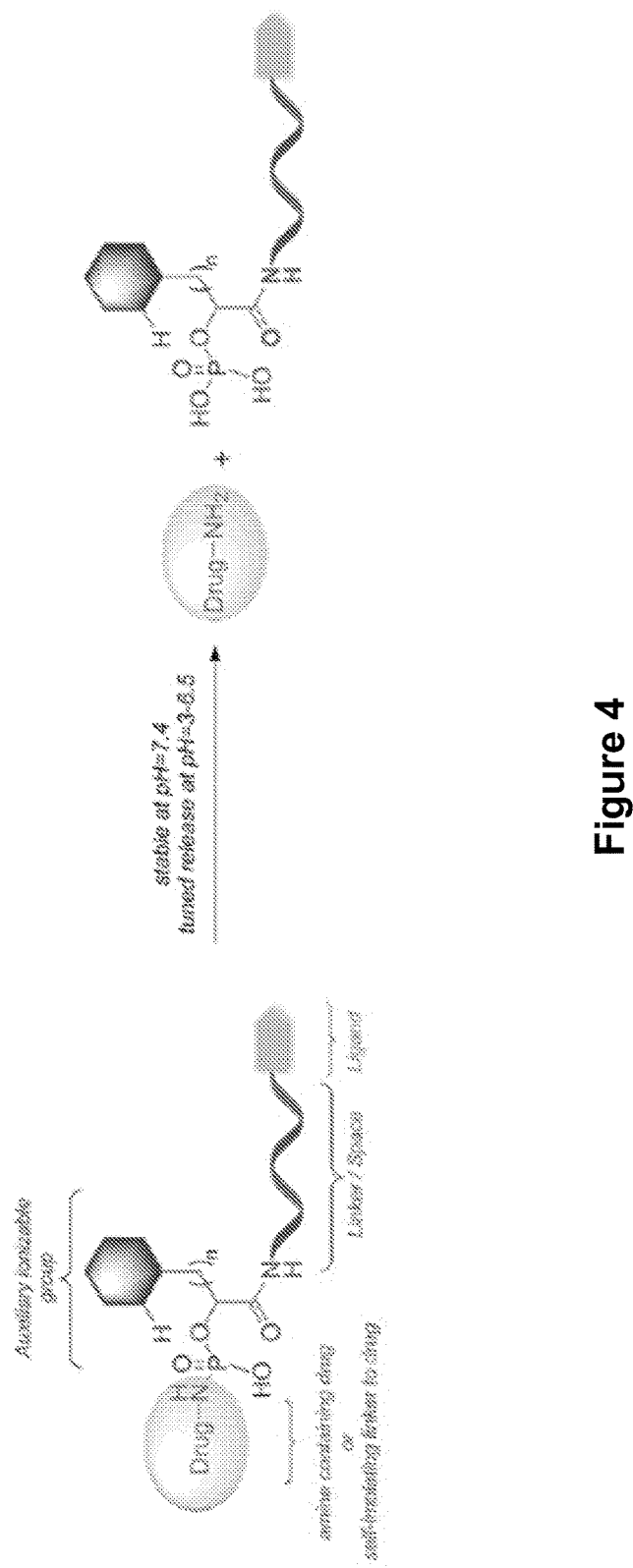
FIG. 4 shows an example of a conjugate for targeted drug delivery.
Figures 5A, 5B:
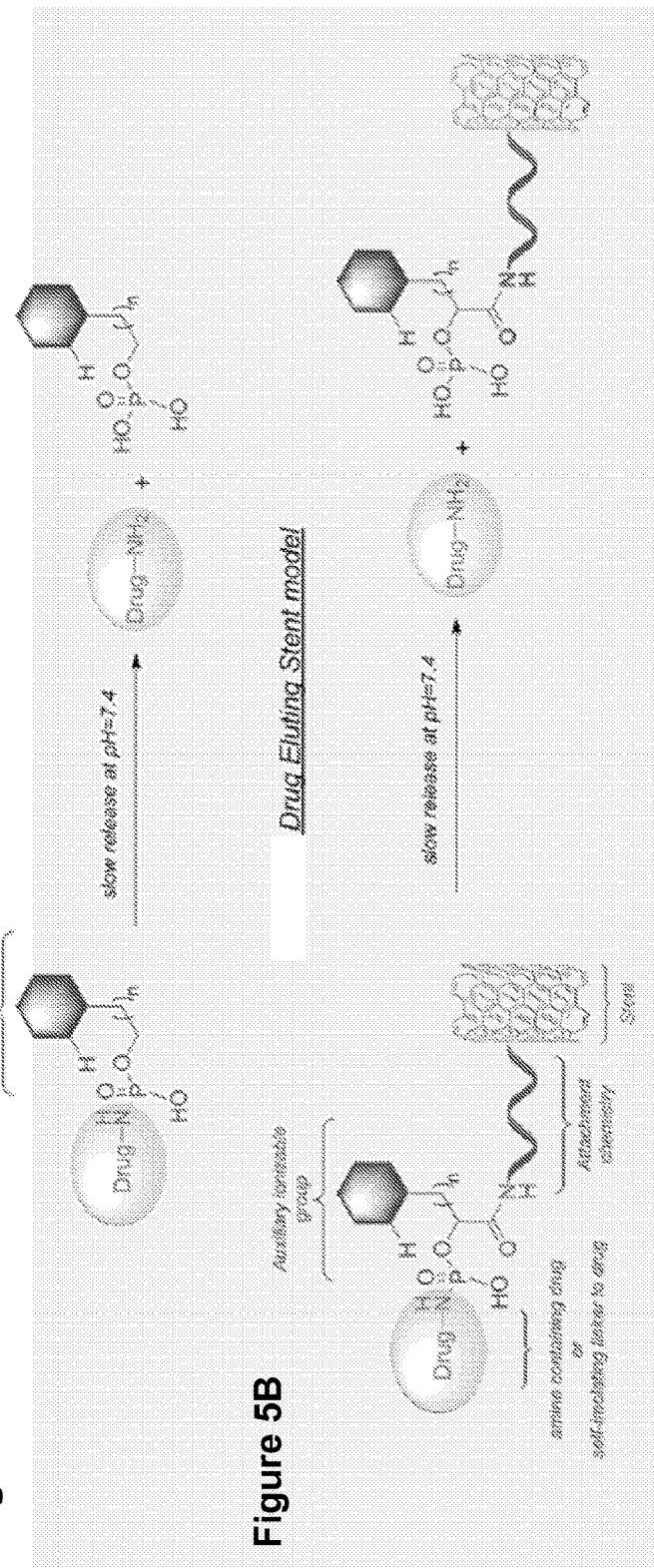
FIG. 5A-5B show examples of conjugates for controlled release: (A) Controlled release of a pro drug and (B) Drug eluting stent.

In the description provided herein, it is understood that a word appearing in the singular encompasses its plural counterpart, and a word appearing in the plural encompasses its singular counterpart, unless implicitly or explicitly understood or stated otherwise. Moreover, the terms used herein unless otherwise specified have the meanings commonly understood by those skilled in the art. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figure(s), as shown herein, are not necessarily drawn to scale, wherein some of the elements may be drawn merely for clarity of the invention.

Additionally, it is to be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Phoshoramidates linked to the side-chain hydroxyl group of serine are unusually labile under pH 6.5 (FIG. 1). Based upon the greater acid stability of phosphoryl hydroxypropylglycine homologs (FIG. 1A), phosphoryl homoserine (FIG. 1B), and phosphoryl serine (FIG. 1C) it was concluded that the alpha-carboxylate of serine promoted the acid sensitivity of O-phosphoryl serine phosphoramidates. This conclusion is further supported by the unusual acid and thermal stability of the hydroxypropyl analog as shown in FIG. 1 in which the alpha-carboxylate is unable to interact with the phosphorus center due to the trans-substitution of the proline ring. The same type of acid sensitivity is observed with an analog that contained a proximal pyridine group compared to those with a phenyl group. From these results, it is assumed that the neighboring ionizable moiety (i.e., alpha-carboxylate or a proximal pyridine group) activates the central phosphoramidate core for hydrolysis of the P—N bond of the linker through internal general acid catalysis.

Furthermore, the phosphoramidate linker scaffold is tunable for pH-triggered and by altering the distance, orientation, and flexibility of the neighboring ionizable moiety to the phosphorus core; increasing this distance results in both increased acid and physiological stability thus enabling predictable and tunable rate of drug release. In addition, altering the pKa of the neighboring ionizable moiety will result in altered rates of drug release. Any 1° or 2° amine-containing drugs may be conjugated to the linker. In addition, alcohol-containing drugs can be coupled to the linker through a self-immolating spacer, thus allowing for a wider range of targeted drug conjugates to be enabled.

The present disclosure provides conjugates comprising an agent covalently attached to a hydrolysable linker. The hydrolysable linker is tunable and sensitive to changes in pH. In one aspect, the linker is stable at physiological pH (about pH 7.4) and will release the attached agent at a lower pH, such as pH 5.5, the endosomal environment of organelles in cancer cells. The release of the agent is rapid and does not require enzymatic action. The drop of the pH triggers the release of the agent. The hydrolysable linker enables targeted delivery of the agent to the site of interest. In another aspect, the agent can be any molecule, such as a diagnostic or therapeutic agent. Additionally, the conjugate can be covalently attached to various targeting molecules, for example antibodies, ligands, and inhibitors, through the linker which enables delivery of wide variety of agents, whether diagnostic or therapeutic, to targeted sites.

The present disclosure provides a conjugate or a salt thereof having formula (I)

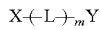
formula (I)

wherein,

X is an agent comprising a moiety for attaching to L or directly to Y,

L is a spacer comprising a moiety for attaching to Y;

m is 0 or 1;

when m is 0,

X comprises a moiety $NR_1$, S, or O for attaching to Y; and $R_1$ is H, acyl, formyl, heterocycloalkyl, substituted or unsubstituted alkyl, substituted or unsubstituted cycloalkyl, substituted or unsubstituted aryl, substituted or unsubstituted heteroaryl, substituted or unsubstituted alkyl-aryl, substituted or unsubstituted cycloalkyl-aryl, substituted or unsubstituted alkyl-heteroaryl, or substituted or unsubstituted cycloalkyl-heteroaryl;

when m is 1,

X comprises $NR_1$, S or O for attaching to L;

L comprises a moiety $NR_1$, S, or O for attaching to Y; and $R_1$ is H, acyl, formyl, heterocycloalkyl, substituted or unsubstituted alkyl, substituted or unsubstituted cycloalkyl, substituted or unsubstituted aryl, substituted or unsubstituted heteroaryl, substituted or unsubstituted alkyl-aryl, substituted or unsubstituted cycloalkyl-aryl, substituted or unsubstituted alkyl-heteroaryl, or substituted or unsubstituted cycloalkyl-heteroaryl;

Y is a hydrolysable linker having formula (II) or formula (III); or

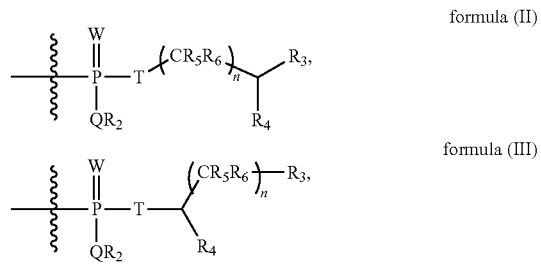

wherein,

W is O, S, or Se;

Q is N, O, S, or Se;

$R_2$ is H, substituted or unsubstituted alkyl, substituted or unsubstituted cycloalkyl, substituted or unsubstituted aryl, substituted or unsubstituted heteroaryl, substituted or unsubstituted alkyl-aryl, substituted or unsubstituted cycloalkyl-aryl, substituted or unsubstituted alkyl-heteroaryl, or substituted or unsubstituted cycloalkyl-heteroaryl;

$R_3$ is an ionizable group;

$R_4$ is H, lower alkyl, aryl, or a substituent comprising a functional group for attachment to a molecule;

$R_5$ and $R_6$ are independently, H, lower alkyl, or aryl;

T is O, S, NH, alkylene, arylene, acyl, formyl, or substituted or unsubstituted alylarylene; and n is 0, 1, 2, 3, 4, 5, 6, 7, 8, or 9.

As used herein, the term "alkyl" refers to a linear or branched, saturated hydrocarbon-based chain containing from 1 to 10 carbon atoms. Examples of alkyls include a methyl group, ethyl group, n-propyl group, isopropyl group, n-butyl group, isobutyl group, s-butyl group, t-butyl group, pentyl group, isopentyl group, 2,3-dimethylpropyl group, 3,3-dimethylbutyl group, and hexyl group. As used herein, the term "substituted alkyl" refers to an alkyl substituted with, for example, but not limited to, a halogen, a alkoxy group, nitro group, cyano group, carboxylic acid, or a hydroxyl group. As used herein, the term "lower alkyl" refers to a linear or branched, saturated hydrocarbon-based chain containing from 1 to 4 carbon atoms.

As used herein, the term "cycloalkyl" refers to a cyclic saturated hydrocarbon-based chain containing from 3 to 8 carbon atoms. As used herein, the term "substituted cycloalkyl" denotes a cyclic saturated hydrocarbon-based chain containing from 3 to 8 carbon atoms and substituted with, for example, but not limited to, a halogen atom, an alkoxy group, nitro group, cyano group, carboxylic acid, or a hydroxyl group.

As used herein, the term "aryl" refers to an aromatic hydrocarbon-based ring or two fused aromatic hydrocarbon-based rings. Examples of aryls include a phenyl group or a naphthyl group. As used herein, the term "substituted aryl" refers to an aromatic hydrocarbon-based ring or two fused aromatic hydrocarbon-based rings which is (are) substituted with one or more groups such as, but not limited to, an alkyl, an alkoxy, an aryl, a halogen, nitro group, cyano group, carboxylic acid, and a hydroxyl.

As used herein, the term "alkyl-aryl" refers to an alkyl substituted with an aryl. As used herein, the term "substituted alkyl-aryl" refers to an alkyl substituted with a substituted aryl.

As used herein, the term "heterocycle" refers to a saturated or unsaturated, cyclic or polycyclic hydrocarbon-based chain comprising one or more heteroatoms, for example, O, S and N. As used herein, the term "substituted heterocycle" refers to a heterocycle substituted with one or more groups of atoms, such as, but not limited to, an alkyl, an alkoxy, a halogen, nitro group, cyano group, carboxylic acid, and a hydroxyl.

As used herein, the term "heteroaryl" refers to an aromatic heterocyclic group, i.e. a cyclic or polycyclic aromatic hydrocarbon-based chain, comprising one or more heteroatoms chosen from O, S and N. As used herein, the term "substituted heteroaryl radical" refers to a heteroaryl substituted with one or more groups of atoms, such as, but not limited to, an alkyl, an alkoxy, an aryl, a substituted aryl, a halogen, and a hydroxyl.

The conjugates, provided herein or a salt thereof, comprise a hydrolysable linker, Y. The hydrolysable linker can have formula (I) or formula (II), as shown above. The hydrolysable linker comprises an ionizable group, $R_3$.

Examples of ionizable groups of $R_3$ include, but are not limited to, ionizable group is selected from the group consisting of a carboxylic acid; an ester of a carboxylic acid; a sulfonic acid; an ester of a sulfonic acid; a phosphoric acid; an ester of a phosphoric acid; a phosphonic acid; an ester of a phosphonic acid; a substituted or unsubstituted aromatic ring containing one or more carboxylic acids, esters of carboxylic acids, sulfonic acids, esters of a sulfonic acids, phosphoric acids, esters of a phosphoric acids, phosphonic acids, and esters of a phosphonic acids, a substituted or unsubstituted heterocyclic aromatic group containing one or more nitrogen atoms; a substituted or unsubstituted fused heterocyclic aromatic group containing one or more nitrogen atoms and containing one or more aromatic or aliphatic rings; a substituted or unsubstituted aniline group; and a substituted or unsubstituted fused aniline group containing one or more nitrogen atoms and containing one or more aromatic or aliphatic rings. In one aspect, the ionizable group of $R_3$ is the ester of the acid as a protected precursor.

The hydrolysable linker is both a pH sensitive linker and a tunable linker. As used herein, the term "pH-sensitive linker" refers to a linker that undergoes hydrolysis at pH values below 7.4. The linker may undergo hydrolysis in the presence, for example, of a Lewis acid or aqueous acid conditions. In one aspect, the conjugate comprising the linker is stable at physiological pH, and undergoes hydrolysis releasing the agent attached to the linker at a specific pH lower than 7.4. In another aspect, the agent is released or the rate of hydrolysis of the linker is faster at a certain pH than at another pH. For example, a linker may undergo accelerated hydrolysis at pH ranging between 3.5-6.5, as compared to a pH ranging between 7-7.5.

As used herein, the term "tunable" refers to the condition under which the linker undergoes hydrolysis may be adjusted based on modifications that may be made to the molecule. As an example, the modification includes increasing the distance between the phosphorus group and the ionizable group, through increasing the number of $(CH_2)_n$ groups between them. In embodiments, the number of $(CH_2)_n$ groups in the linker can range from 0 to 20, in which case n is 0 to 20 for $(CH_2)_n$. In other embodiments, n is 0 to 9 for $(CH_2)_n$. Additionally, the linker is tunable by altering the pKa of the ionizable group by well-known methods, such as changing the substituents. As an example, when the ionizable group is a pyridine, adding substituents to the pyridine ring will alter the pKa of the pyridine nitrogen. If the ionizable group is on an aromatic ring (such as a benzoic acid), adding substituents to the ring will change the pKa of the carboxylic acid.

The conjugate provided herein is useful for delivering the attached agent to a desired site. The conjugate, provided by the present disclosure, comprises an agent, X. X comprises a $NR_1$, S, or O for attaching to Y directly or through a spacer, L. In an embodiment, X comprises S or O for attaching to the spacer to enable release of the agent from the spacer. X can also comprise $NR_1$, S, or O for attaching to the spacer. In other embodiments, X comprises any functional group for attaching to L.

The agent can be any molecule that need to be delivered to a targeted site. As an example, the agent can be a diagnostic agent or a therapeutic agent.

Diseases are often diagnosed using imaging studies such as magnetic resonance imaging (MRI), magnetic resonance tomography (MRT), positron emission tomography (PET), computer tomography (CT), single-photon emission computed tomography (SPECT) and optical imaging, such as x-ray. Imaging agents include agents used in imaging studies.

Diagnostic agents are detectable or traceable labels. Examples of diagnostic agents used in these studies include, but are not limited to, radioisotopes, dyes (including those using a biotin-streptavidin complex), enzymes, contrast agents, fluorescent compounds or molecules such as a fluorescent dye, paramagnetic ions (for MRI), and small molecules including both inorganic and organic small molecules that target cell surface receptors or otherwise bind to the surface or other accessible intracellular or extracellular components of tumor cells.

The diagnostic agent include any suitable label or detectable group detectable by optical, spectroscopic, photochemical, biochemical, immunochemical, electrical, optical or chemical means including but not limited to biotin, dyes, fluorophores, antigens, porphyrins, chromophores, and radioactive isotopes. Diagnostic agents include, but are not limited to, radiolabels (e.g., $^{35}S$, $^{125}I$, $^{32}P$, $^{3}H$, $^{14}C$, $^{131}I$), radioacoustic labels, enzyme labels (e.g., horseradish peroxidase, alkaline phosphatase), gold beads, chemiluminescence labels, ligands (e.g., biotin, digoxin) and/or fluorescence labels (e.g., rhodamine, phycoerythrin, fluorescein, fluorescent proteins), a fluorescent protein including, but not limited to, a green fluorescent protein or one of its many modified forms, a nucleic acid segment in accordance with known techniques, and energy absorbing and energy emitting agents. Examples of labels include biotin for staining with labeled avidin or streptavidin conjugate, magnetic beads (e.g., Dynabeads™), fluorescent dyes (e.g., fluorescein, fluorescein-isothiocyanate (FITC), Texas red, rhodamine, green fluorescent protein, enhanced green fluorescent protein, lissamine, phycoerythrin, near-IR dye, Cy2, Cy3, Cy3.5, Cy5, Cy5.5, Cy7, FluorX (Amersham), and SyBR Green I & II (Molecular Probes)), radiolabels (e.g., $^{35}S$, $^{125}I$, $^{32}P$, $^{3}H$, $^{14}C$, $^{131}I$), enzymes (e.g., hydrolases, particularly phosphatases such as alkaline phosphatase, esterases and glycosidases, or oxidoreductases, particularly peroxidases such as horseradish peroxidase), substrates, cofactors, inhibitors, chemiluminescent groups, chromogenic agents, and calorimetric labels such as colloidal gold or colored glass or plastic (e.g., polystyrene, polypropylene, latex, etc.) beads. Other diagnostic agents include examples of common isotopes used for example in Nuclear Medicine. Such isotopes include but are not limited to $^{11}C$, $^{18}F$, $^{99m}Tc$, $^{64}Cu$, $^{111}In$, $^{123}I$, $^{68}Ga$.

A therapeutic agent is an atom or molecule that is useful in the treatment of a disease. The term "therapeutic agent" and "drug" are used interchangeably in this specification. Examples of therapeutic agents include chemotherapeutic agents, antibodies, antibody fragments, toxins, enzymes, nucleases such as a ribonuclease (RNase), or DNase I, hormones, cytokines, angiogenesis inhibitors, antisense oligonucleotides, small interfering RNA (siRNA), chelators, boron compounds, photoactive agents, small molecules, and radioisotopes.

A chemotherapeutic agent includes, for example, an anti-cancer agent, an antineoplastic agent, and a cytotoxic agent. Examples of anti-cancer chemotherapeutic agents include, but are not limited to, 5-fluorouracil, bleomycin, busulfan, camptothecins, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, methotrexate, mitomycin, navelbine, nitrosurea, plicamycin, procarbazine, raloxifene, tamoxifen, TAXOL, temazolomide (an aqueous form of DTIC), transplatinum, vinblastine and methotrexate, vincristine, or any analog or derivative variant of the foregoing. Chemotherapeutic agents of use against infectious organisms include, but are not limited to, acyclovir, albendazole, amantadine, amikacin, amoxicillin, amphotericin B, ampicillin, aztreonam, azithromycin, bacitracin, BACTRIM, BATRAFEN, bifonazole, carbenicillin, caspofungin, cefaclor, cefazolin, cephalosporins, cefepime, ceftriaxone, cefotaxime, chloramphenicol, cidofovir, Cipro®, clarithromycin, clavulanic acid, clotrimazole, cloxacillin, doxycycline, econazole, erythrocycline, erythromycin, FLAGYL®, fluconazole, flucytosine, FOSCARNET®, furazolidone, ganciclovir, gentamycin, imipenem, isoniazid, itraconazole, kanamycin, ketoconazole, lincomycin, linezolid, meropenem, miconazole, minocycline, naftifine, nalidixic acid, neomycin, netilmicin, nitrofurantoin, nystatin, oseltamivir, oxacillin, paromomycin, penicillin, pentamidine, piperacillin-tazobactam, rifabutin, rifampin, rimantadine, streptomycin, sulfamethoxazole, sulfasalazine, tetracycline, tioconazole, tobramycin, tolciclate, tolnaftate, trimethoprim sulfamethoxazole, valacyclovir, vancomycin, zanamir, and zithromycin.

A cytotoxic agent is a substance that inhibits or prevents the function of cells and/or causes destruction of cells. Examples of such agents include radioactive isotopes (for example, $At^{211}$, $I^{131}$, $I^{125}$, $Y^{90}$, $Re^{186}$, $Re^{188}$, $Sm153$, $Bi^{212}$, $P^{32}$, and radioactive isotopes of Lu); enzymes and fragments thereof such as nucleolytic enzymes; antibiotics; and toxins such as small molecule toxins or enzymatically active toxins of bacterial, fungal, plant or animal origin, including fragments and/or variants thereof.

Examples of toxins include but are not limited to bacterial toxin, a plant toxin, ricin, abrin, Staphylococcal enterotoxin-A, pokeweed antiviral protein, gelonin, diphtherin toxin, Pseudomonas exotoxin, Pseudomonas endotoxin, Ranpirnase (Rap) and Rap (N69Q).

Hormones can be used as a therapeutic agent themselves or in combination with other chemotherapeutic agents. Progestins, such as hydroxyprogesterone caproate, medroxyprogesterone acetate, and megestrol acetate, have been used in cancers of the endometrium and breast. Estrogens such as diethylstilbestrol and ethinyl estradiol have been used in cancers such as prostate cancer. Antiestrogens such as tamoxifen have been used in cancers such as breast cancer. Androgens such as testosterone propionate and fluoxymesterone have also been used in treating breast cancer. Corticosteroid hormones such as prednisone and dexamethasone can improve the effective of other chemotherapeutic agents.

Cytokines that are used as therapeutic agents include, but are not limited to, lymphokines, monokines, growth factors, and polypeptide hormones. Examples of cytokines include but are not limited to human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, tumor necrosis factor-α, tumor necrosis factor-β, mullerian-inhibiting substance, mouse gonadotropin-associated peptide, inhibin, activin, vascular endothelial growth factor, integrin, thrombopoietin (TPO), NGF-.beta., platelet-growth factor, TGF-α, TGF-β, insulin-like growth factor-I, insulin-like growth factor-II, erythropoietin (EPO), osteoinductive factor, interferon-α, interferon-β, interferon-γ, macrophage-CSF (M-CSF), granulocyte-macrophage-CSF (GM-CSF), granulocyte-CSF (G-CSF), IL-1, IL-1 α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, LIF, kit-ligand, FLT-3, angiostatin, thrombospondin, endostatin, and lymphotoxin.

Examples of angiogenesis inhibitors that are used as therapeutic agents include, but are not limited to, angiostatin, baculostatin, canstatin, maspin, anti-VEGF antibodies, anti-PIGF peptides and antibodies, anti-vascular growth factor antibodies, anti-Flk-1 antibodies, anti-Flt-1 antibodies and peptides, laminin peptides, fibronectin peptides, plasminogen activator inhibitors, tissue metalloproteinase inhibitors, interferons, interleukin-12, IP-10, Gro-.beta., thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4, and minocycline.

Examples of small molecules for use as therapeutic agents include, but are not limited to, abrin, amantadine, amoxicillin, amphotericin B, ampicillin, aplidin, azaribine, anastrozole, azacytidine, aztreonam, azithromycin, bacitracin, trimethoprim/sulfamethoxazole, Batrafen, bifonazole, bleomycin, bortezomib, bryostatin-1, busulfan, calicheamycin, camptothecin, 10-hydroxycamptothecin, carbenicillin, caspofungin, carmustine, cefaclor, cefazolin, cephalosporins, cefepime, ceftriaxone, cefotaxime, celecoxib, chlorambucil, chloramphenicol, ciprofloxacin, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, diphtheria toxin, DNase I, doxorubicin, 2-pyrrolinodoxorubicine (2P-DOX), doxycycline, cyano-morpholino doxorubicin, doxorubicin glucuronide, epirubicin glucuronide, ethinyl estradiol, estramustine, estrogen receptor binding agents, etoposide, etoposide glucuronide, etoposide phosphate, erythrocycline, erythromycin, flagyl, farnesyl-protein transferase inhibitors, floxuridine (FUdR), 3',5'-O-dioleoyl-FudR (FUdR-dO), fludarabine, flutamide, fluorouracil, fluoxymesterone, ganciclovir, gentamycin, gelonin, gemcitabine, hydroxyprogesterone caproate, hydroxyurea, idarubicin, ifosfamide, isoniazid, itraconazole, kanamycin, ketoconazole, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, minocycline, naftifine, nalidixic acid, neomycin, navelbine, nitrosurea, nystatin, ranpirnase, oxacillin, paromomycin, penicillin, pentamidine, piperacillin-tazobactam, phenyl butyrate, prednisone, procarbazine, paclitaxel, pentostatin, pokeweed antiviral protein, PSI-341, semustine, rifabutin, rifampin, rimantadine, streptomycin, sulfamethoxazole, sulfasalazine, streptozocin, tamoxifen, taxanes, taxol, testosterone propionate, tetracycline, thalidomide, thioguanine, thiotepa, teniposide, topotecan, transplatinum, trimethoprim sulfamethoxazole, uracil mustard, valacyclovir, vancomycin, vinblastine, vinorelbine, vincristine, zanamir, and zithromycin.

The conjugate disclosed herein or a salt thereof can comprise a radionuclide which is attached to the linker through a peptide or protein. Radionuclide therapy involves controlling or eliminating cancerous growth by irradiating the area containing the growth. Internal radionuclide therapy involves administering a small radiation source, such as a gamma or beta emitter, to a target area, Iodine-131 is commonly used to treat thyroid cancer. Iridium-192 implants are used especially in the head and breast. Lutetium-177 dotatate or octreotate is used to treat tumors such as neuroendocrine ones, and the carrier attaches to the surface of the tumor.

Targeted Alpha Therapy (TAT) or alpha radioimmunotherapy involves targeting a radionuclide such as Bi-213 lead-212 to the right place using a carrier such as a monoclonal antibody. Examples of cancers that may be treated using TAT include leukemia, cystic glioma, pancreatic, ovarian, and melanoma cancers.

In embodiments, therapeutic agents for attachment to the conjugates disclosed herein include therapeutic agents for the treatment of cancer and non-cancer therapeutic agents. These therapeutic agents include organic small molecules: including all hydroxyl and amine-containing therapeutic agents for the treatment of cancer, for example, molecules that inhibit the replication of DNA (e.g., Doxorubicin, Epirubicin, Calecheamicin, Camptothecin), molecules that stabilize or disrupt microtubules (e.g., Paclitaxel, Docetaxel, Epothilone), molecules that affect the $Na^+/K^+$ pump (e.g., Strophanthidin), molecules that affect the function of the Golgi apparatus (e.g., Norrisolide and active derivatives of Norrisolide). These therapeutic agents also include inorganic small molecules, such as all hydroxyl and amine containing therapeutic agents for the treatment of cancer, for example, cisplatin or oxoplatin. Examples of linked antitumor agents include, for example, CO-Doxorubicin, and CO-Strophanthidin.

In other embodiments, the therapeutic agents for attachment to the conjugates disclosed herein include but are not limited to proteins: including proteins of human and non-human origin, for example, antibodies (e.g. trastuzumab), hormones (e.g. leutinizing hormone, follicle stimulating hormone), cytokines (e.g. IL-6), growth factors (e.g. G-CSF), bacterial or plant toxins (e.g., *Pseudomanas* toxin, gelonin, ricin, abrin) and tumor-targeting soluble proteins of any type; peptides including engineered and natural peptides that are toxic to tumor cells, that alter the architecture or function of such cells, or target other molecules to tumor cells or cells in the tumor that serve to support tumor cells, for example, lysins, TAT-related proteins that enhance cell penetration; nucleic acids such as RNA, for example, antisense RNA, silencing RNA, toxin aptamers, DNA such as naturally-occurring and synthetic oligonucleotides and higher molecular weight structures, for example, plasmid and viral vectors that express RNAs or proteins that are toxic to tumor cells; particles such as polymer-derived, protein-derived, metal-derived and inorganic-based particles of any size, for example, nanoparticles loaded with therapeutic agents, detectable labels or imaging agents such as fluorescent dyes or radionuclides; small molecules such as both inorganic and organic small molecules that target cell surface receptors or otherwise bind to the surface or other accessible intracellular or extracellular components of tumor cells.

Therapeutic agents also include drugs that are active in the CNS, for example, L-Dopa, Ritalin, Cymbalta, Namenda, and Gleevec.

In other embodiments, the therapeutic agent of the disclosed conjugate is an anticancer agent, an antineoplastic agent, or a cytoxic molecule. In one aspect, the therapeutic agent is selected from the group consisting of an amine group containing antineoplastic agent say, for example, monomethylauristatin E (MMAE), monomethylauristatin F (MMAF), and doxorubicin.

It is to be understood that the agents attached may actually be a derivative, with modifications at the linking site. For example, the agents can be modified to comprise an amine group, a sulfur atom, or an oxygen atom for attaching to the hydrolysable linker. The amine group can be a $NR_1$ as described previously. Moreover, as an example, the agent can be attached to a spacer comprising an amine group for attaching to the linker. The agent can be linked directly to the hydrolysable linker. The agent can also be attached to the linker through a spacer (L). The spacer can range in length from 2 to 30 atoms. The spacer can be short and remain attached to the drug after releasing from the linker. The spacer can be linear or branched and can contain heteroatoms. The spacer can contain a substituted or unsubstituted aromatic ring. The spacer can comprise or can be a self-immolating spacer or a self immolating spacer used in tripartate prodrug or mutual prodrug strategies. The spacer can comprise an $NR_1$ ($R_1$ is as described above), a sulfur atom, or an oxygen atom for attaching to the linker. The spacer can be a peptide or a protein. Specific examples of spacers include those disclosed in the references of Alouane et al. (Angewandte Chemie, 2015, 54, 7492-7509), Nareshkumar et al. (Pharmaceutical Research, published March 2015, http://link.springer.com/article/10.1007/s11095-015-1657-7), Tranoy-Opalinski et al. (Medicinal Chemistry, 2008, 8, 618-637), and Sheng (http://www2.chemistry.msu.edu/courses/cem958/FS13_SS14%5CWei_Sheng.pdf). All of which are incorporated by reference in their entirety.

The conjugate disclosed herein comprises a $R_4$ group. In embodiments, the $R_4$ is a H. In other embodiments, the $R_4$ is a substituent comprising a functional group for attachment to a molecule. The functional group can be a chemical and/or bioorthogonal functional group for example, an amino group, an amide group, an azide, alkyne, maleimide, iodoacetamide, thiol, disulfide, and NHS ester.

The term "biorthogonal chemistry" refers to a chemical reaction that can occur inside of living systems without interfering with native biochemical processes. Bioorthogonal reactions proceed in high yield under physiological conditions and result in covalent bonds between reactants that are otherwise stable in these settings. Bioorthogonal reactions are reactions of materials with each other, wherein each material has limited or substantially no reactivity with functional groups found in vivo. For example, the efficient reaction between an azide and a terminal alkyne, i.e., the most widely studied example of "click" chemistry, is known as a useful example of a bioorthogonal reaction. Click chemistry refers to a group of reactions that generate substances quickly and reliably and provide high product yields.

The functional group of $R_4$ could be any chemical functionality that is part of a click chemistry pair or a chemical motif that results from the reaction with an azide, alkyne, maleimide, iodoacetamide, thiol, disulfide, NHS ester, or a click chemistry pair. Examples of bioorothogonal click chemistry pair include azide/alkyne, (ketone or aldehyde)/(hydrazine or hydrazide), and tetrazine/cyclooctene. The bioorothogonal click chemistry pair might be a thioacid and a chemical motif for native chemical ligation, or an azide and a chemical motif for a Staudinger ligation. The Staudinger ligation (or Staudinger reduction) is a chemical reaction in which the combination of an azide with a phosphine or phosphite produces an iminophosphorane intermediate.

The conjugate disclosed herein can further comprise a molecule attached to the functional group of $R_4$. The molecule can be a targeting molecule, a solid support, an attachment handle, or a masking agent. Examples of attachment handle include but are not limited to maleimide, azide, alkyne, NHS ester, and thiol. Examples of a masking agent include but are not limited to PEG pegylation of varying length to block immune recognition or a group to improve stability and ester of a carboxylic acid that can be hydrolyzed by changes in pH or by the action of enzymes. The molecule can be linked to the functional group of $R_4$ through a spacer. The spacer can comprise or can be a self-immolating spacer or a non-self immolating spacer.

The conjugates provided herein also comprises a targeting molecule covalently attached through the functional group of $R_4$. The targeting molecule has the ability to specifically and stably bind to an external receptor and/or binding site of a molecule on an outer surface of a cell. The cell is a target of interest. For example, the cell is a cell of the tumor vasculature and/or a cancer cell, wherein the external receptor and/or binding site is specific for the cell of the tumor vasculature and/or cancer cell (i.e., is uniquely expressed or overexpressed on a luminal surface of the cell of a tumor vasculature or cancer cell).

Examples of targeting molecule include, but are not limited to, ligands, antibodies, proteins, peptides, peptidomimetics, aptamers, enzyme inhibitors, biomarkers, or substrates.

The ligand can be a ligand that binds to a receptor expressed on cells to be targeted. Examples of receptors that may be targeted by conjugates provided herein include urokinase receptor, epidermal growth factor (EGF) receptor, insulin-like growth factor receptor, interleukin-4 (IL-4) receptor, interleukin 6 (IL-6) receptor, keratinocyte growth factor (KGF) receptor, platelet-derived growth factor (PDGF) receptor, fibroblast growth factor (FGF) receptor, laminin receptor, vascular endothelial growth factor (VEGF) receptor, transferrin receptor, phosphatidylserine (PS), fibronectin, and the like, as well as portions thereof, and variants thereof, that substantially maintain the ability to bind to the ligand attached to the conjugate.

Examples of targeting molecules attached to the conjugates provided herein include, but are not limited to, RGD-peptide homing ligand, epidermal growth factor, vascular endothelial growth factor, 2-[3(1,3-dicarboxypropyl)-ureido]pentanedioic acid (DUPA), targeting prostate specific membrane antigen (PSMA), lectin, estrogen, polyunsaturated fatty acid (e.g., linoleic acid, linolenic acid, arachidonic acid, eicosapentaenoic acid), carbohydrate, non-peptide, vitamin, steroidal estrogen, biotin, riboflavin, nutrient-transport molecule (such as, but not limited to, transferrin), or any other cell binding molecule or substance thereof having the ability to bind to or reactively associate or complex with an antigen, a receptor or other receptive moiety present on a surface of a particular cell so that the ligand can function to target the conjugate to the desired cell. As an example, the desired cell may be an infected cell, a bacterial or other type of pathogenic cell, a transformed cell, a tumor cell, a metastatic cell, a cell that produce autoimmune antibodies associated with an autoimmune disease, a cell that engages in modulating immune responses, wherein the antigen or receptor is uniquely expressed or overexpressed on the surface of the infected cell, bacterial cell, tumor cell, etc., and thus "marks" the cell as being an infected cell, bacterial cell, tumor cell, etc. The targeting molecule may be a ligand for the cell surface receptor and bind in a binding groove of the receptor. Also, the targeting molecule may be an antibody or fragment thereof raised against an epitope comprising a portion of the cell surface receptor, and capable of binding to the receptor when it is expressed on the surface of a cell of interest.

The targeting molecule and the agents can be covalently attached to the linker of formula (II) or (III) using chemical synthesis that are routinely practiced including bioorthogonal reactions. The targeting molecule and agents can be attached to the linker through spacers.

As an example, the conjugates provided herein is a conjugate or a salt thereof have formula (IV)

A conjugate or a salt thereof having formula (IV)

wherein,

X is an agent comprising a moiety for attaching to L or directly to Y,

L is a spacer comprising a moiety for attaching to Y;

m is 0 or 1;

when m is 0,

X comprises a moiety $NR_1$, S, or O for attaching to Y; and $R_1$ is H, acyl, formyl, heterocycloalkyl, substituted or unsubstituted alkyl, substituted or unsubstituted cycloalkyl, substituted or unsubstituted aryl, substituted or unsubstituted heteroaryl, substituted or unsubstituted alkyl-aryl, substituted or unsubstituted cycloalkyl-aryl, substituted or unsubstituted alkyl-heteroaryl, or substituted or unsubstituted cycloalkyl-heteroaryl;

when m is 1,

X comprises $NR_1$, S or O for attaching to L;

L comprises a moiety $NR_1$, S, or O for attaching to Y; and $R_1$ is H, acyl, formyl, heterocycloalkyl, substituted or unsubstituted alkyl, substituted or unsubstituted cycloalkyl, substituted or unsubstituted aryl, substituted or unsubstituted heteroaryl, substituted or unsubstituted alkyl-aryl, substituted or unsubstituted cycloalkyl-aryl, substituted or unsubstituted alkyl-heteroaryl, or substituted or unsubstituted cycloalkyl-heteroaryl;

Y is a hydrolysable linker having formula (V) or formula (VI)

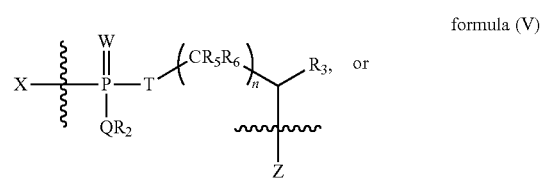

formula (V)

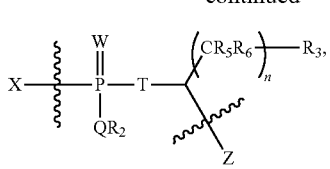

formula (VI)

wherein,
W is O, S, or Se;
Q is N, O, S, or Se;
$R_2$ is H, substituted or unsubstituted alkyl, substituted or unsubstituted cycloalkyl, substituted or unsubstituted aryl, substituted or unsubstituted heteroaryl, substituted or unsubstituted alkyl-aryl, substituted or unsubstituted cycloalkyl-aryl, substituted or unsubstituted alkyl-heteroaryl, or substituted or unsubstituted cycloalkyl-heteroaryl;
$R_3$ is an ionizable group;
$R_5$ and $R_6$ are independently, H, lower alkyl, or aryl;
T is O, S, NH, alkylene, arylene, acyl, formyl, or substituted or unsubstituted alylarylene;
n is 0, 1, 2, 3, 4, 5, 6, 7, 8, or 9; and
Z is selected from a solid support, targeting molecule, attachment handle, or masking agent, optionally linked through a non-self immolating spacer.

In embodiments, the conjugate or a salt thereof has the formula (IV), wherein the therapeutic agent is an antineoplastic agent for prostate cancer say for example, MMAE and the targeting molecule is the prostate specific membrane antigen (PSMA).

In other embodiments, the hydrolysable linker in the conjugate provided herein may comprise a functional group, for example an amide group or amino group, for attachment to another molecule (see Example 5). This attachment could be any common functional group that results in the coupling of two functional groups, for example, an amide connection would come from an amine from the drug conjugate portion and the carboxylate from the targeting molecule or vice versa. These attachments can also involve, but not limited to click chemistry coupling pairs, metal-mediate ligations, and disulfide bonds. As an example, the molecule can be a targeting molecule or a detectable label. The conjugate can further comprise a chemical and/or biorthogonal functional group and a functional group (amide group or amino group) attached to the hydrolysable linker. Optionally, a spacer can be inserted between the chemical and/or biorthogonal functional group and the functional group attached to the hydrolysable linker. In this embodiment, a targeting molecule or a detectable label can be attached to the conjugate through the functional group attached directly to the hydrolysable linker or through the bioorthogonal group.

Figure 9:
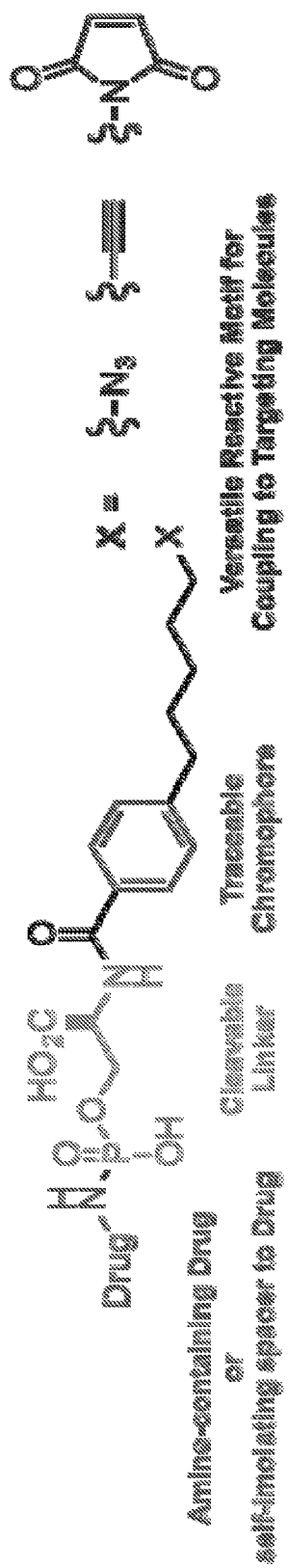
FIG. 9 shows an example of a drug conjugate assembly containing a traceable chromophore.
Figure 10A:
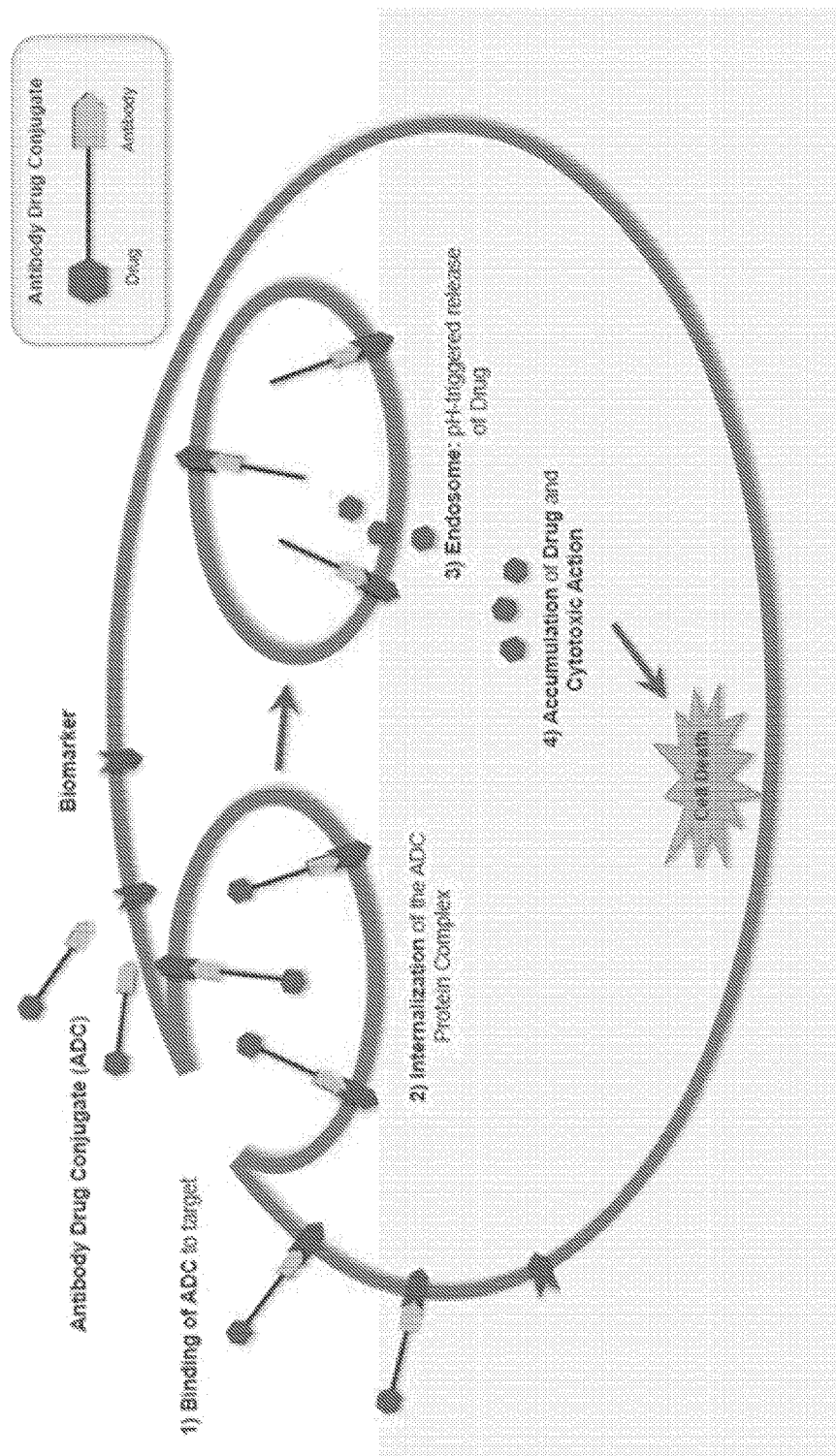
FIGS. 10A-10B show application of a pH-tunable linker in an antibody-drug conjugate (ADC).
Figure 10B:
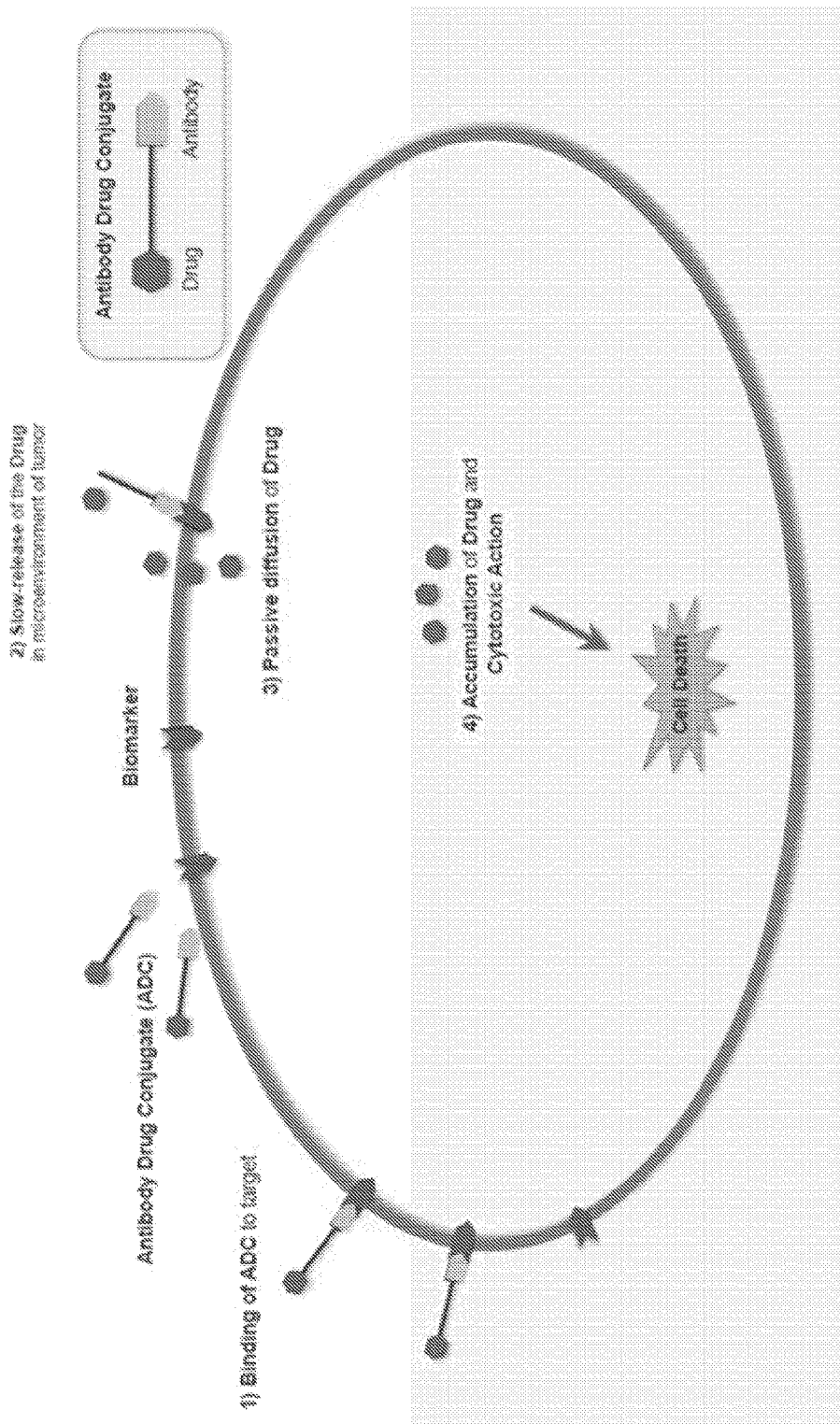
Figure 11:
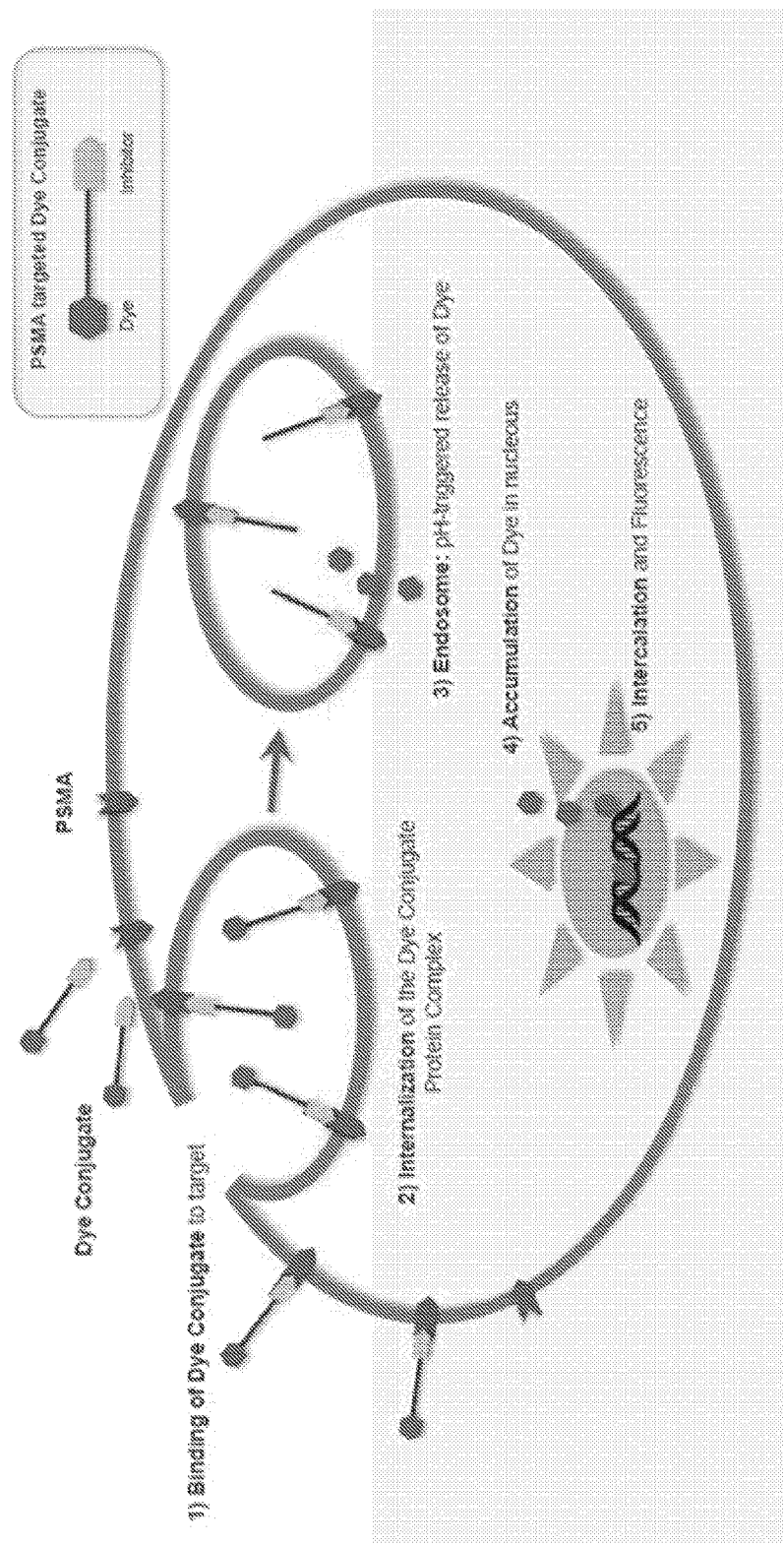
FIG. 11 shows application of a pH-tunable linker in a fluorescent dye conjugate.

In embodiments, the conjugate disclosed herein can further comprise a detectable or traceable label, dye, or chromophore attached to the ionizable group. An example of such a conjugate is shown in FIG. 9. Further, the conjugate disclosed herein can further comprise a detectable label, dye, or chromophore attached at the $R_4$ position. In each embodiment, the detectable label, dye, or chromophore can further comprise a chemical and/or bioorthogonal functional group mentioned above for attaching a targeting molecule. The detectable label, dye, or chromophore can be attached to the functional group through a spacer.

In one aspect, the conjugates provided herein comprise a spacer inserted between the agent (X) and the hydrolysable linker (Y). In another aspect, the conjugates provided herein comprises a spacer attached to the $R_4$ of the hydrolysable linker. The conjugates provided herein can comprise a spacer attached indirectly to the ionizable group ($R_3$) through a functional group. The spacer attached to $R_3$ and $R_4$ groups can be used for attachment to a molecule or to a chemical or bioorthogonal functional group for clicking to a molecule. The molecule can be a targeting molecule, a polymer, or a solid support.

Also provided herein are methods of synthesizing a conjugate comprising a pH-sensitive linker and agent, comprising the steps of obtaining the linkers of formula (II) and (III) and covalently attaching a therapeutic or diagnostic agent. The method may further comprise attaching a molecule such as a targeting molecule to the conjugate. The conjugates are synthesized by conventional chemical reactions which are routinely performed to attach a linker to an agent, such reactions include but are not limited the Atherton-Todd reaction and modifications thereof.

Provided herein are salts and pharmaceutically acceptable salts of the conjugates of formula (I) or (IV). The term "pharmaceutically acceptable salt" refers to a salt of a compound that does not cause significant irritation to an organism to which it is administered and does not abrogate the biological activity and properties of the compound. In some embodiments, the salt is an acid addition salt of the conjugate. Pharmaceutical salts can be obtained by reacting the conjugate with inorganic or organic acid. Pharmaceutical salts can also be obtained by reacting the conjugate with a base to form a salt of the conjugate.

The present disclosure provides compositions comprising the disclosed conjugate having formula (I) or (IV) or a salt thereof. The composition can comprise an excipient, a carrier, an adjuvant, stabilizer, or a diluent.

Provided herein are also pharmaceutical compositions comprising the disclosed conjugate having formula (I) or (IV) or a salt thereof. The pharmaceutical composition can comprise a pharmaceutically acceptable excipient, carrier, adjuvant, stabilizer, or diluent. Pharmaceutically acceptable carriers to be included are determined by the composition being administered and by the method of administering the composition. There are a wide variety of suitable formulations of pharmaceutical composition including optional pharmaceutically acceptable carriers, excipients, stabilizers, etc.

In some embodiments, the pharmaceutical composition comprising the conjugate disclosed herein can include one or more physiologically acceptable surface active agents, carriers, diluents, excipients, smoothing agents, suspension agents, film forming substances, and coating assistants, or a combination thereof; and a compound (e.g., a polymer conjugates described herein) disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical compositions disclosed herein may be manufactured by means of conventional mixing, dissolving, granulating, dragee-making, levigating, emulsifying, encapsulating, entrapping or tableting processes. The pharmaceutical compositions can be prepared as liquid solutions or suspensions, solid forms suitable for solution or suspension in liquid prior to use, or as emulsions.

Additionally, the conjugates in the pharmaceutical compositions are contained in an amount effective to achieve its intended purpose. As used herein, the term "effective amount" is used to refer to an amount of an active conjugate that provides an intended purpose. For example, the effective amount may be a diagnostically effective amount for diagnostic purposes. The effective amount may be a therapeutically effective amount for preventing, alleviating, or ameliorating symptoms of disease or prolong the survival of the subject being treated.

Determination of an effective amount is dependent upon various factors. The effective amount of the conjugate disclosed herein required as a dose will depend on the route of administration, the type of subject being treated, and the physical characteristics of the specific animal under consideration. The dose can be tailored to achieve a desired effect, but will depend on such factors as age, weight, diet, the severity of the affliction, concurrent medication and other factors. The determination of effective dosage levels, that is the dosage levels necessary to achieve the desired result, can be accomplished by one skilled in the art using routine methods, for example, human clinical trials and in vitro studies.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

As an example, chemotherapeutic agents and methods of administration, dosages, etc., are well known to those of skill in the art (see for example, the "Physicians Desk Reference", Goodman & Gilman's "The Pharmacological Basis of Therapeutics" and in "Remington's Pharmaceutical Sciences", incorporated herein by reference in relevant parts). Some variation in dosage will necessarily occur depending on the condition of the subject being treated. The person responsible for administration will, in any event, determine the appropriate dose for the individual subject.

There are various manner for administering the conjugates disclosed herein including, but not limited to, oral, rectal, topical, aerosol, injection, and parenteral delivery, including intramuscular, subcutaneous, intravenous, intramedullary injections, intrathecal, direct intraventricular, intraperitoneal, intranasal, transmucosal, and intraocular injections.

Provided herein are also kits comprising the disclosed conjugates having formula (I) or (IV) for use in the laboratory or for prognostic, prophylactic, diagnostic and therapeutic applications. Such kits can comprise a package or container that is compartmentalized to receive one or more containers such as vials, tubes, and the like, each of the container(s) comprising one of the separate elements to be used in the method, along with a label or insert comprising instructions for use, such as a use described herein. The conjugate can be placed in one compartment and liquids or other components for preparing the conjugate for use can be placed in a separate compartment.

As an example, the pharmaceutical compositions can be presented in a pack or dispenser device which can contain one or more unit dosage forms containing the conjugate. The pack may for example comprise metal or plastic foil, such as a blister pack. The pack or dispenser device can be accompanied by instructions for administration. Compositions that can include a conjugate described herein formulated in a compatible pharmaceutical carrier may also be prepared, placed in an appropriate container, and labeled for treatment of an indicated condition.

The present disclosure provides methods of using the conjugates disclosed herein for delivering the attached agent to desired sites. The conjugates disclosed herein provides a combination of site specific recognition and therapeutic effect at the local site. The conjugates provided herein can be used as ligand-therapeutic agent, antibody-therapeutic agents, drug eluting stents/implants, nanoparticle based delivery system, and polymer based delivery system. The agents attached to the conjugates can be delivered under sustained release or immediate release at a specific site. The acidity of the environment can be used to trigger release via hydrolysis. The therapeutic agents attached to the conjugates can be tuned to release, for example, in endosomes, tumor microenvironments, and inflamed tissued, which have an acidic environment.

The agents linked to the conjugates provided herein can utilize the lower intracellular or extracellular pH (for example, pH 4.5, pH 5.0, pH 5.5, between about pH 4.5 and 7, between about pH 5 and 6, between about pH 5.2 and 5.8, between about 5.5 and 6, between about 6 and 6.9, between about 6.2 and 6.8, or between about 6.4 and 6.9) of some tumor cells, compared to that of blood or normal tissues, to trigger the release of the therapeutic agents from suitable targeting or delivery systems that are stable at physiological pH but can be hydrolyzed to release an amine containing therapeutics at a lower pH; wherein the conjugate hydrolyzes more rapidly at pH values below 7.4.

Figure 7:
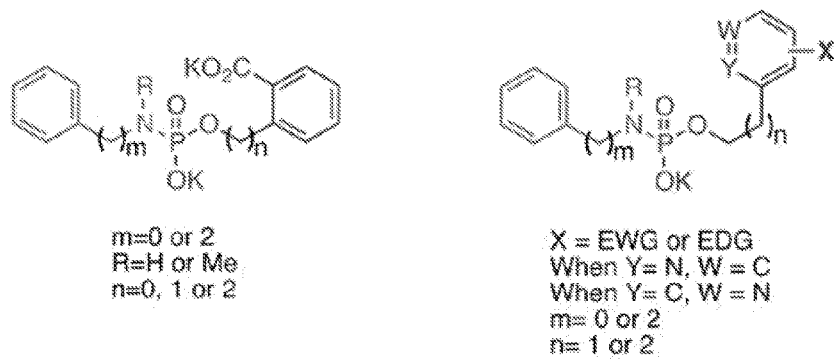
FIG. 7 shows examples of tuning pKa of an ionizable group. EWG is an electron withdrawing group, and EDG is an electron donating group.

The rate of hydrolysis of the conjugate can be tuned via steric effects using bulky neighboring groups to inhibit attack of the reactive center or via electronic effects using electron withdrawing or donating groups in immediate proximity to the reactive center to tune the pKa of the reactive center. As an example, FIG. 7 provides possible modifications for tuning the pKa of the ionizable group. Accordingly, the rate of hydrolysis of the conjugates provided herein can be tuned by varying the substituents in the neighboring group, by varying the distance between the ionizable group and the phosphorus center, and by the flexibility (rotation around bonds) of the chemical structure between the ionizable group and the phosphorus center. As an example, if the ionizable group is linked to the phosphorus center through a trans- or cis-double bond, there would be limited degrees of freedom for rotation around the bonds between the ionizable group and the phosphorus center. Moreover, the distance between the agent and the phosphrous center can varied for tuning the hydrolysis of the conjugates.

Provided herein are methods of using the disclosed conjugates for diagnostic and therapeutic purposes. The present disclosure also provides methods of using the disclosed conjugates for treating and diagnosing patients.

In embodiments, the present disclosure provides methods of treating or ameliorating a disease or condition that can include administering an effective amount of one or more of the conjugates described herein or one or more of the pharmaceutical compositions described herein to a subject in need thereof. In other embodiments, the conjugates provided herein are used to deliver an anticancer drug to a selected tissue. In other embodiments, the conjugates provided herein can be used to form a medicament that can be used to treat or ameliorate a disease or condition. The disease or condition can be a cancer such as lung cancer, breast cancer, colon cancer, ovarian cancer, prostate cancer, and melanoma. The disease or condition can be a tumor selected from the group consisting of lung tumor, breast tumor, colon tumor, ovarian tumor, prostate tumor, and melanoma tumor.

Figure 8:
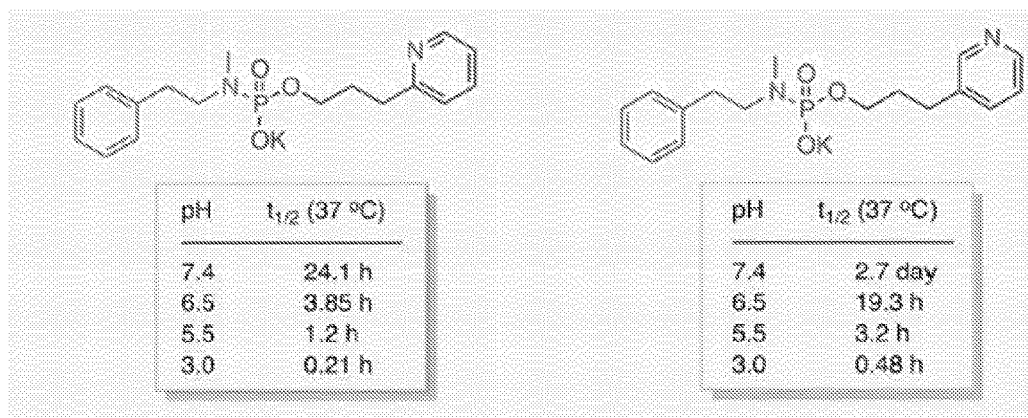
FIG. 8 shows plasma stability of cleavable linkers with the desired release profile.

When a conjugate is administered to a subject in vivo, its plasma stability is important. The present disclosure provides conjugates with the desired plasma stability. Plasma stability of cleavable linkers with the desired release profile are provided herein. Examples of desired release profile of conjugates are shown in FIG. 8.

Figure 6:
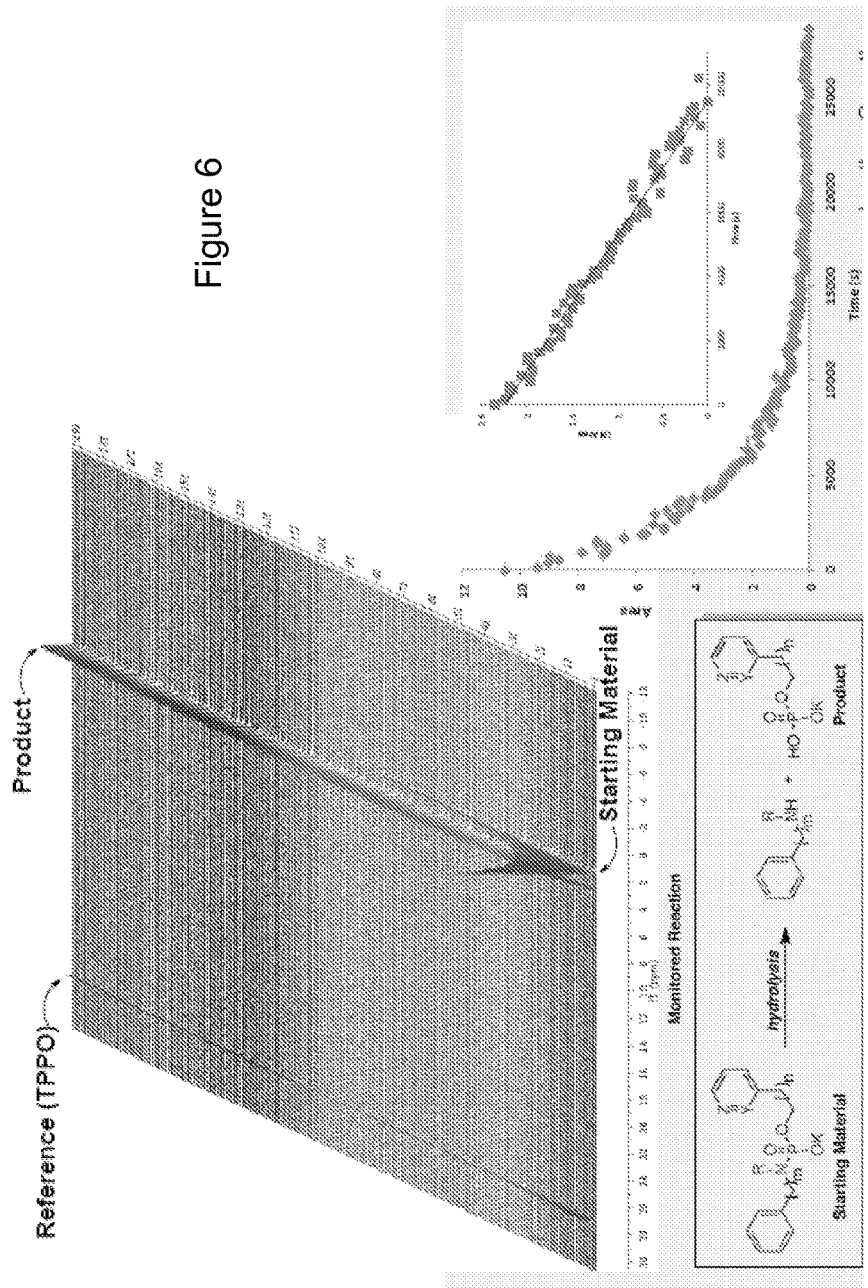
FIG. 6 shows pH stability studies using NMR to monitor hydrolysis.

The present disclosure provides a method of screening for conjugates that can deliver an agent at a specific pH. In one aspect, conjugates having formula (I) comprising various substituents neighboring the ionizable group and having varying length between the ionizable group and the phosphorus center could be screened to determine which conjugates will hydrolyze at pH 3.0, 3.5, 4.0, 4.5, 5.0, 5.5, 6.0, and 6.5. In another aspect, a specific conjugate can be screened to determine at which pH it will hydrolyze or which pH its rate of hydrolysis is the fastest. The hydrolysis of the conjugate can be monitored by nuclear magnetic resonance (NMR) (FIG. 6), HPLC, spectrophotometric methods, or mass spectrometry.

The present disclosure provides methods of reporting different pH environments by releasing or activating a detectable label such as a flourescent dye in a FRET probe.

In an embodiment, the method provided herein comprises (a) obtaining a conjugate having formula (I); (b) placing the conjugate in an environment in which the pH is less than 7.4; and (c) detecting the release of the agent. In other embodiments, the method provided herein comprises (a) obtaining a conjugated having formula (I); (b) placing the conjugate having formula (I) in an environment in which the pH is 7.4; (c) lowering the pH; and (d) detecting release of the agent.

The phrase "consisting essentially of" means that the conjugates, compositions, and methods provided herein include the recited elements and exclude other elements of essential significance to the combination for the stated purpose. Therefore, a conjugate, composition, or method consisting essentially of the elements as defined herein would not exclude other components, materials, or steps that do not materially affect the basic and novel characteristic(s) of the claimed invention.

The following examples illustrate exemplary methods provided herein. These examples are not intended, nor are they to be construed, as limiting the scope of the disclosure. It will be clear that the methods can be practiced otherwise than as particularly described herein. Numerous modifications and variations are possible in view of the teachings herein and, therefore, are within the scope of the disclosure.

EXAMPLES

Example 1

During the development and evaluation of various phosphoramidate scaffolds, it was observed that phoshoramidates linked to the side-chain hydroxyl group of serine were unusually labile under pH 6.5. Based upon the greater acid stability of phosphoryl homoserine (FIG. 1B) and phosphoryl hydroxpropylglycine (FIG. 1A) homologs, it was concluded that the alpha-carboxylate of serine promoted the acid lability of O-phosphoryl serine phosphoramidates (FIG. 1C). It was recognized that this unique pH-sensitive nature of phosphoramidates derived from serine was ideally suited to pH-triggered cleavage in endosomes and lysosomes.

A novel pH-sensitive linker (FIG. 2) that is able to trigger the release of a drug from a targeting molecule in targeted drug-conjugate has been synthesized. The linker is stable at physiological pH (7.4) but rapidly releases the drug at pH 5.5, which is the environment of endosomal organelles in cancer cells. Targeted chemotherapy generally involves the use of a targeting molecule linked to a drug. The linker is superior to current linkers used in targeted chemotherapy such as antibody-drug conjugates (ADCs) because the drug release is rapid, requiring no enzymatic action. Only the drop in pH from 7.4 to 5.5 is required to trigger the release of the drug after the drug conjugate is internalized into cells. In addition, the linker is tunable for releases at lower pH values by increasing the distance (n) between the phosphorus center and the carboxylic acid ($HO_2C$) in the linker. The linker is also versatile in that it is amenable to being coupled to a wide variety of targeting molecules (e.g., antibodies, small molecule ligands and inhibitors).

In model experiments, it was found that the novel linker was stable at pH 7.4 but rapidly hydrolyzed to release an amine-containing payload (representing an amine-containing drug) at pH 5.5 (FIG. 3A). A linker missing the alpha-carboxylic acid from the serine scaffold was shown to be stable under the same conditions (FIG. 3B). These data support the effectiveness and promise of this novel linker in targeted drug conjugate scaffolds.

Example 2

Exemplary linkers are synthesized as shown in Schemes 1-3 and described below.

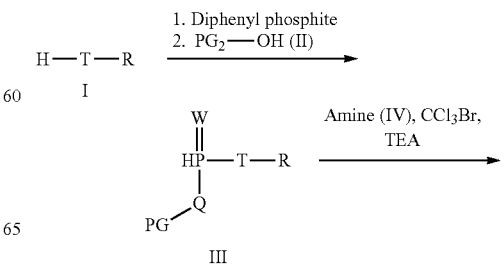

Scheme 1: Synthesis of Phosphite (III) and Phosphoramidate (V)

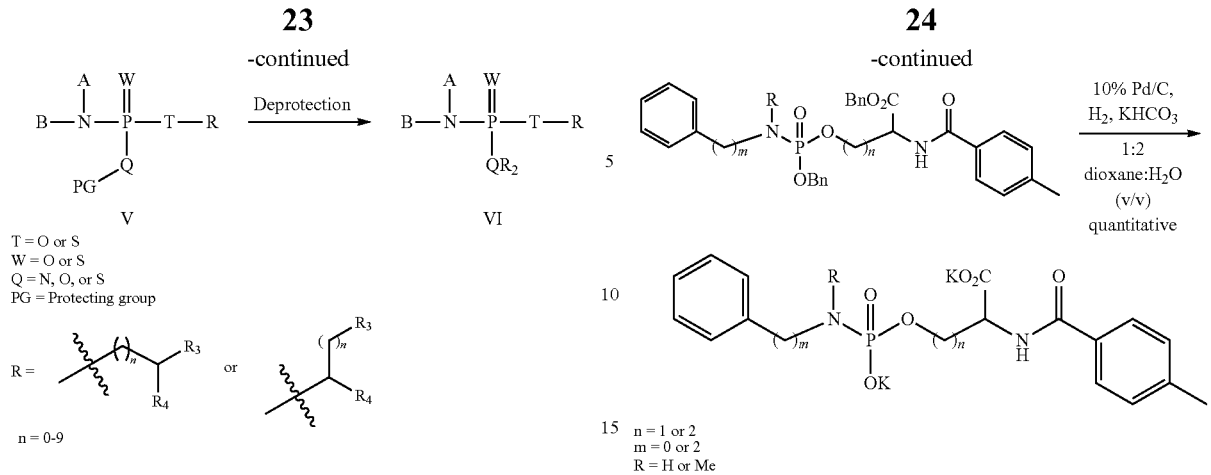

T = O or S
W = O or S
Q = N, O, or S
PG = Protecting group

R = n = 0-9

A and B independently are hydrogen; alkyl; substituted or unsubstituted aryl; or substituted or unsubstituted heteroaryl.

General Procedure for Synthesis of Phosphite (III):

Readily available alcohol I (0.529 mmol) in 2 mL of freshly distilled pyridine was added dropwise via cannula to a stirring solution of diphenylphosphite (0.634 mmol) in 3 mL of freshly distilled pyridine. The resulting solution was stirred for 2 hrs under a stream of Ar(g), followed by the dropwise addition of alcohol II (1.587 mmol) via syringe. The reaction was stirred overnight. The crude mixture was taken up with 25 mL of EtOAc and extracted with 10% copper sulfate (wt/v) until the pyridine has been removed. The organic was washed with dd $H_2O$, followed by brine and dried with $MgSO_4$, filtered and concentrated down to yield a crude oil. The phosphite III was obtained via silica column using EtOAc:Hex as the eluent and taken on to the next step without further purification.

General Procedure for Phosphoramidate (V):

The phosphite III (0.119 mmol) was dissolved in distilled ACN (2 mL) and $CCl_3Br$ (1 mL) and stirred for 15 mins at −15° C. Amine IV (0.125 mmol) in distilled ACN and TEA (0.369 mmol) was added dropwise. Upon completion, the reaction was concentrated down to yield an oil. The crude was taken up in 50 mL of EtOAc and the organic layer was extracted with 1 N HCl (2×, 25 mL), followed by 10% NaHCO3 (2×, 25 mL) and brine (1×, 25 mL), dried with MgSO4, filtered and concentrated down. The product was obtained via prep-Si chromatography.

Carboxylic acid based and pyridine based exemplary linkers were synthesized according to Schemes 2 and 3, respectively.

Scheme 2: Synthesis of Carboxylic Acid Based Exemplary Linkers

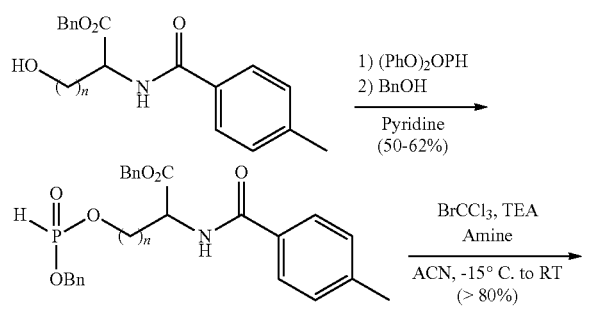

Scheme 3: Synthesis of Pyridine Based Exemplary Linkers

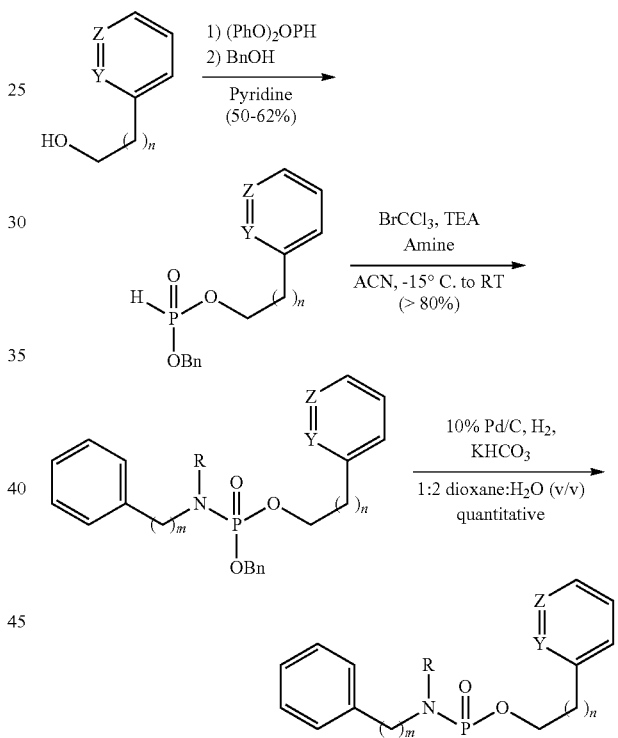

n = 1 or 2
Y = N; Z = C
Y = C; Z = N
m = 0 or 2
R = H or Me

Example 3

It was observed from studies on distance effects that proximity of a neighboring, but electronically isolated, functional group, can be used to alter the stability of a phorphoramidate bond. The stability data obtained with carboxylic acid based exemplary linkers and pyridine based linkers are shown in Tables 1 and 3. Table 2 summarizes the distance effect of carboxylic acid linkers that were studied.

TABLE 1
Exemplary Carboxylic Acid Based Linkers
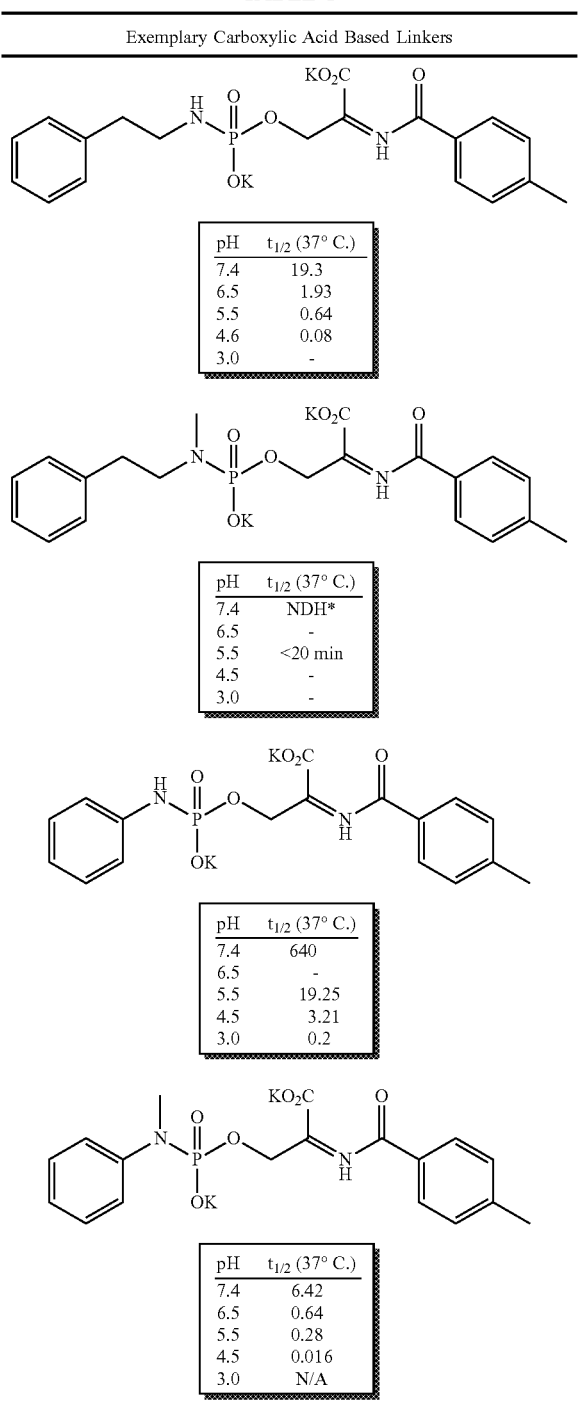
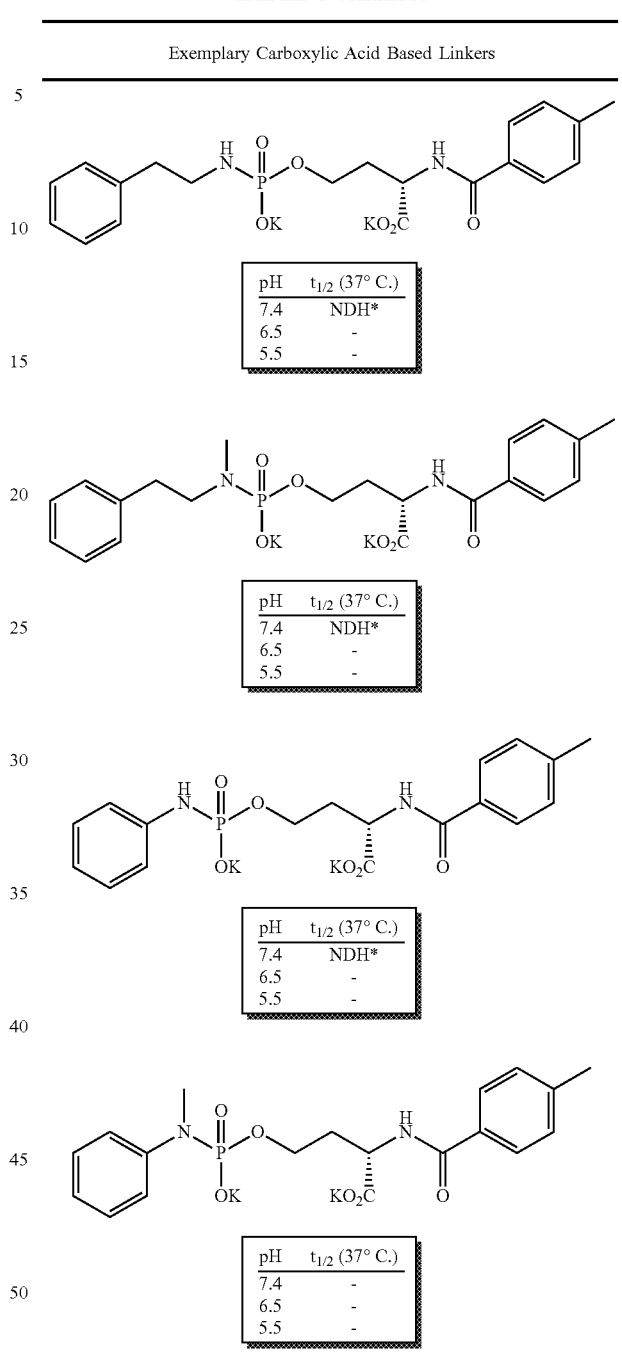
*No detectable hydrolysis after 8 hrs TABLE 2
Distance Effects
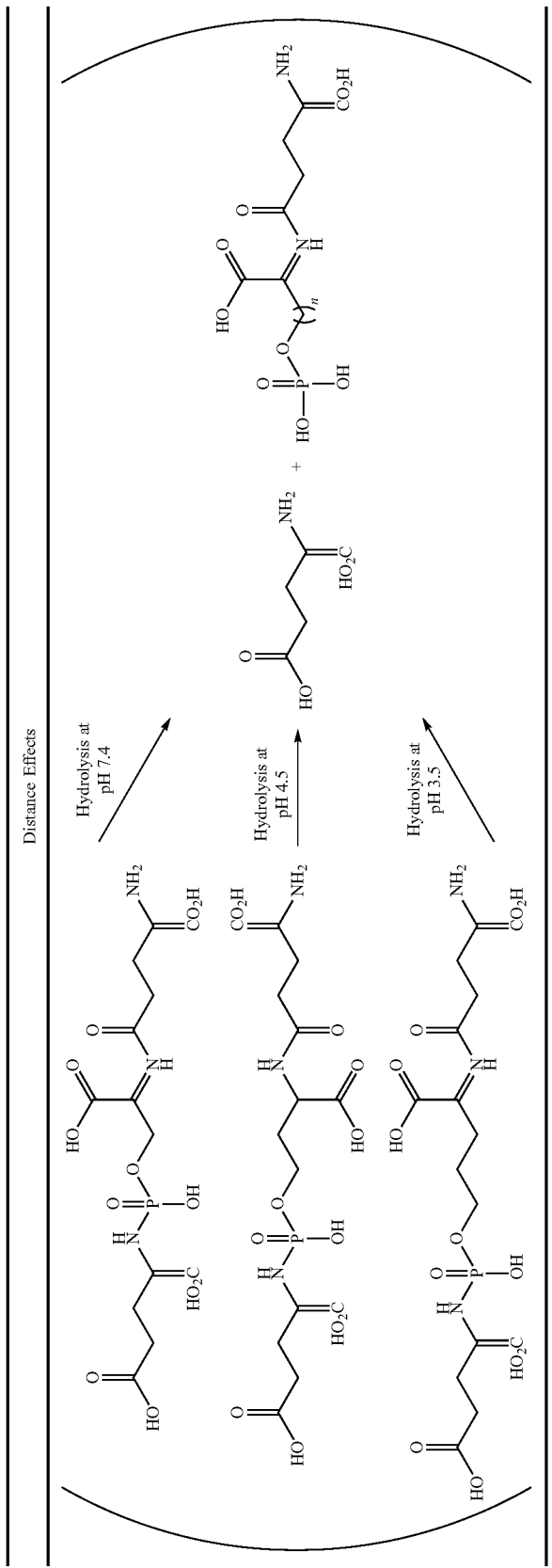

TABLE 3

Stability of Exemplary Pyridine and Carboxylate Based Linkers

| Entry | Structure | ½ Lives for P—N Bond Hydrolysis | | | | |
|---|---|---|---|---|---|---|
| | | pH 3 | pH 4.5 | pH 5.5 | pH 6.5 | pH 7.4 |
| H119 | 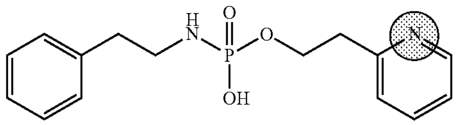 [SMILES: O=P(O)(NCCc1ccccc1)OCCc1ccccn1] | Unstable | | 0.13 hr | 0.32 hr | 2.1 hr |
| H97 | 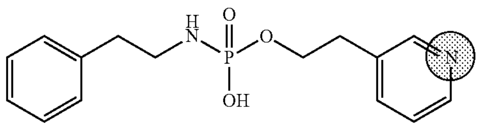 [SMILES: O=P(O)(NCCc1ccccc1)OCCc1cccnc1] | 2.8 hr | | 1.6 days | 4 days | 16 days |
| H41 | 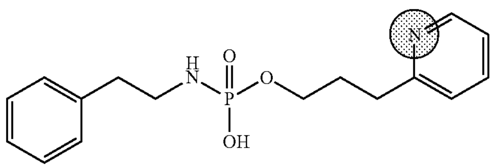 [SMILES: O=P(O)(NCCc1ccccc1)OCCCc1ccccn1] | 2.1 hr | 9.63 hr | 19.3 hr | 24.1 hr | 11 days |
| H5 | 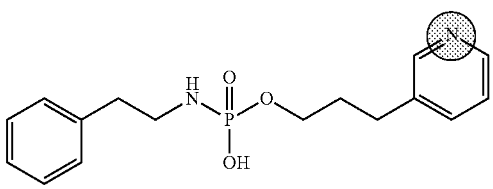 [SMILES: O=P(O)(NCCc1ccccc1)OCCCc1cccnc1] | 1.9 hr | 19.3 hr | 8 day | Stable | 90 day |
| H69 | 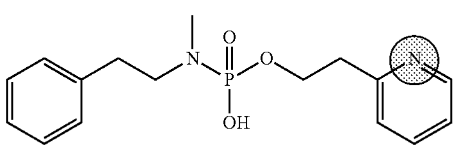 [SMILES: CN(CCc1ccccc1)P(=O)(O)OCCc1ccccn1] | Unstable | Unstable | Unstable | Unstable | Unstable |
| H99 | 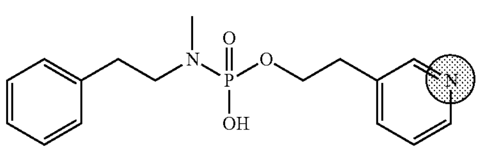 [SMILES: CN(CCc1ccccc1)P(=O)(O)OCCc1cccnc1] | 0.39 hr | 1.93 hr | 3.2 hr | 9.6 hr | 1.6 days |
| H43 | 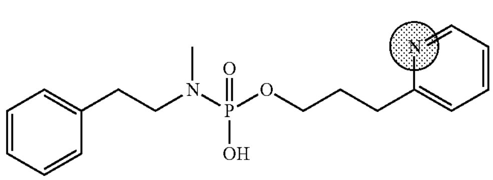 [SMILES: CN(CCc1ccccc1)P(=O)(O)OCCCc1ccccn1] | 0.21 hr | | 1.2 hr | 3.85 hr | 21.4 hr Plasma: 19.3 hr (pH 7.38) |
| H9 | 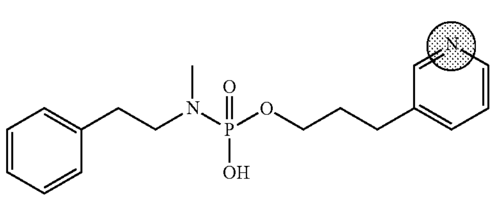 [SMILES: CN(CCc1ccccc1)P(=O)(O)OCCCc1cccnc1] | 0.48 hr | | 3.2 hr | 19.3 hr | 2.7 day Plasma: 27.5 hr (pH 7.23) |

TABLE 3-continued
Stability of Exemplary Pyridine and Carboxylate Based Linkers
| Entry | Structure | ½ Lives for P—N Bond Hydrolysis | | | | |
|---|---|---|---|---|---|---|
| | | pH 3 | pH 4.5 | pH 5.5 | pH 6.5 | pH 7.4 |
| H133 | 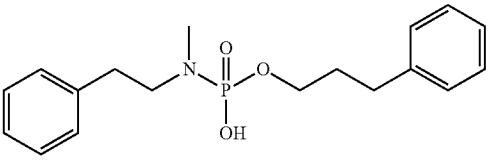 [SMILES: CN(CCc1ccccc1)P(=O)(O)OCCCc1ccccc1] | | | 9.6 hr (1.9 hr) | | |
| H45 | 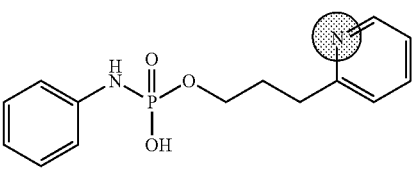 [SMILES: O=P(O)(Nc1ccccc1)OCCCc1ccccn1] | 1.6 day | 8.9 day | 2.0 days | 8 days | 4 day |
| H7 | 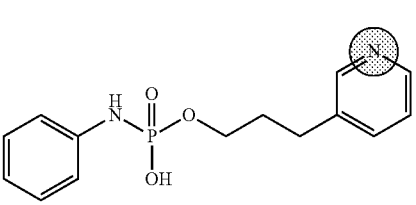 [SMILES: O=P(O)(Nc1ccccc1)OCCCc1cccnc1] | 1.6 day | 133 days Stable | 16 day | 8 day STABLE | 27 day |
| H85 | 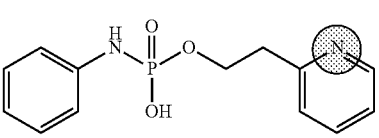 [SMILES: O=P(O)(Nc1ccccc1)OCCc1ccccn1] | 0.32 hr | | 0.96 hr | 1.9 hr | 9.6 hr |
| H113 | 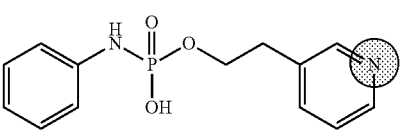 [SMILES: O=P(O)(Nc1ccccc1)OCCc1cccnc1] 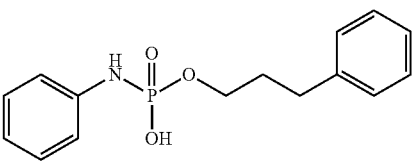 [SMILES: O=P(O)(Nc1ccccc1)OCCCc1ccccc1] | 4 days | 20 days | 8 days | 2 Days Stable | 16 days |
| H135 | 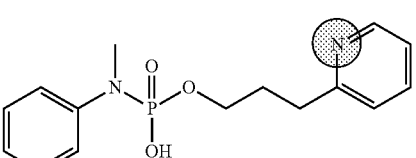 | 0.48 hr | | 2.1 hr | 3.9 hr | 1.3 days |
| H11 | 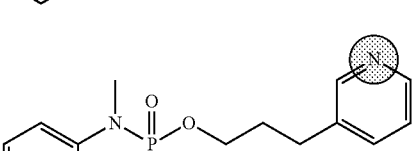 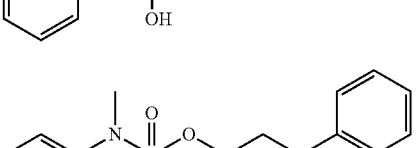 | 0.48 hr | | 9.6 hr | 1.1 days | 10 day |

TABLE 3-continued

Stability of Exemplary Pyridine and Carboxylate Based Linkers

| | | ½ Lives for P—N Bond Hydrolysis | | | | |
|---|---|---|---|---|---|---|
| Entry | Structure | pH 3 | pH 4.5 | pH 5.5 | pH 6.5 | pH 7.4 |
| H115 | | Unstable | Unstable | Unstable | Unstable | Unstable |
| H105 | | 0.64 hr | 3.85 hr | 9.6 hr | 19.3 hr | 10 days |
| H155 | | N/A | N/A | 3.98 min | 9.63 min | 1.93 hr |
| H157 | | N/A | 5.25 min | 38.5 min | 1.93 hr | 19.3 hr |
| H159 | | 12.8 min | 3.21 hr | 19.25 hr | 2.0 days | 26.7 days |
| H161 | | N/A | 0.98 min | 16.5 min | 38.5 min | 6.42 hr |
| H179 | | | 0.96 hr | 9.62 hr | | 2 Days |
| I11 | | | | 14.4 min | 57.8 min | 6.42 hr |

Initial studies yielded, a library of model compounds with a range of kinetic control of hydrolysis.

Example 4

Drug-linker conjugates were synthesized according to Schemes 4 and 5 and described below. Scheme 4 shows synthesis of exemplary drug-linker conjugates. In Scheme 5, a self-immolating spacer is inserted between the drug and the linker. The self-immolating spacer provides the amine group for attaching to the linker and for providing distance for tuning the hydrolysis of the conjugate or release of the drug moiety.

Scheme 4: Synthesis of Exemplary Drug-Linker Congjugates

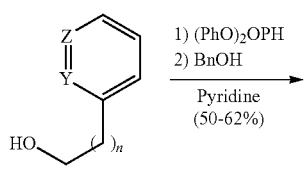

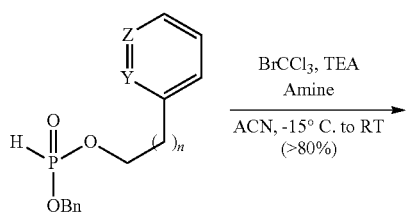

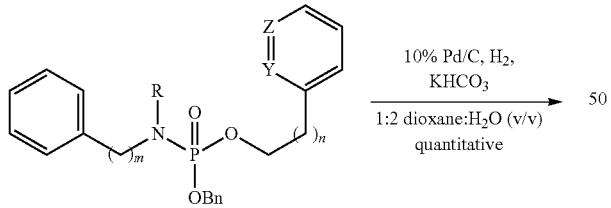

Scheme 5: A Self-Immolating Spacer for Non-Amine Drugs

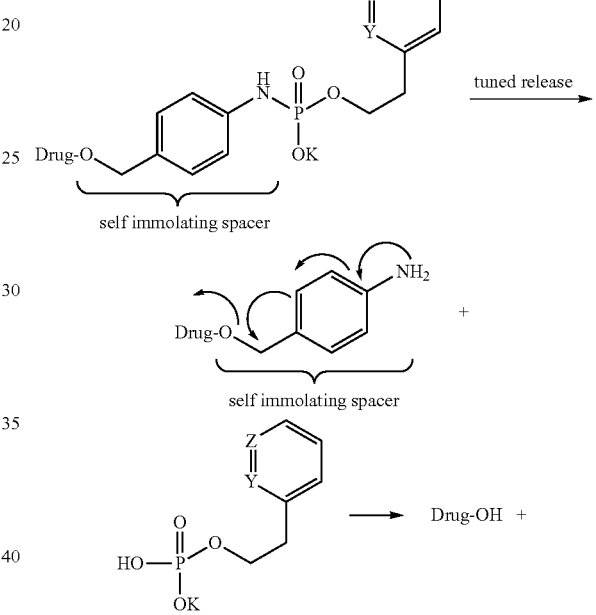

n = 1 or 2
Y = N; Z = C
Y = C; Z = N
m = 0 or 2
R = H or Me

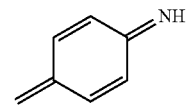

Example 5

Examples of drug-linker conjugates comprising MMAE as the drug and maleimide, or azide as the were synthesized and investigated. Their half-lives are shown in Table 4.

TABLE 4

Examples of Drug-Linker Conjugates-MMAE maleimide or azide

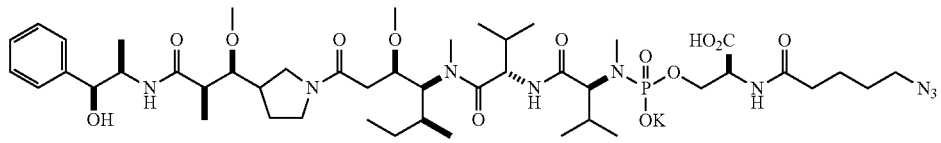

| pH | $t_{1/2}$ (37° C.) |
|---|---|
| 7.4 | NDH* |
| 6.5 | - |
| 5.5 | <20 min |

TABLE 4-continued

Examples of Drug-Linker Conjugates-MMAE maleimide or azide

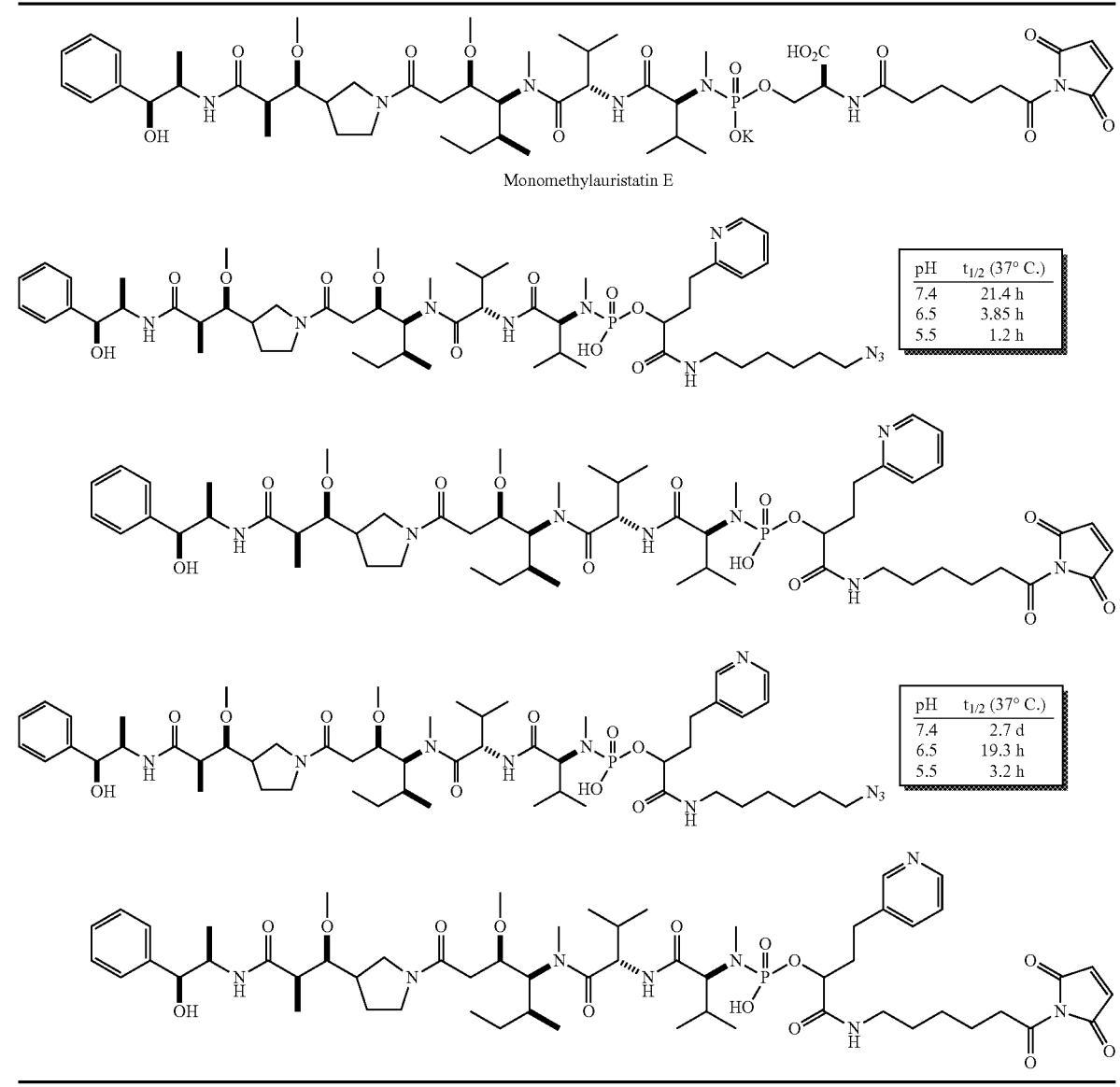

Monomethyllauristatin E

Example 6

Monomethyl auristatin E (MMAE) is a synthetic anticancer agent. However, because of its toxicity, MMAE cannot be administered by itself. MMAE has to be directed to the cancer cells through a targeting molecule. Cancer cells express specific antigens or biomarkers. Targeting molecules, such as antibodies and binding agents, have been developed to specifically bind the antigens or biomarkers on cancer cells.

The biomarker for prostate cancer is PSMA (prostate-specific membrane antigen). TG97 is a PSMA inhibitor analog that binds PSMA.

For targeted chemotherapy of prostate cancer, a drug-PSMA targeting molecule conjugate (Scheme 5) has been synthesized by "click" chemistry. It has been shown that the conjugate effectively and rapidly homes to PSMA-expressing tumors in vivo. The conjugate was "clicked" to radio-isotopes ($^{64}$Cu and $^{99m}$Tc) bearing a click-ready azide group in order to observe the delivery of the drug to PSMA expressing prostate tumors.

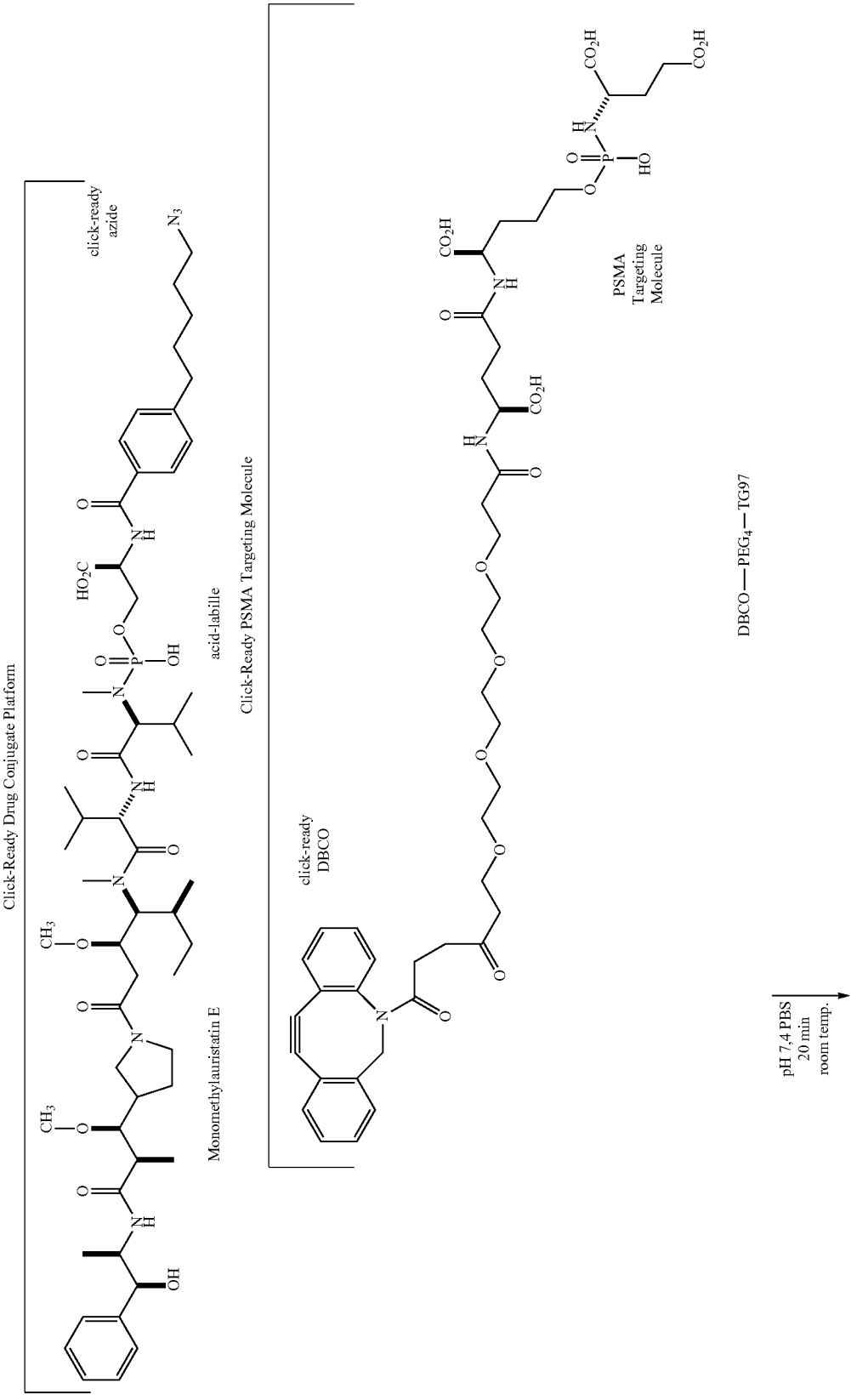
Scheme 5: PSMA-Targeted Drug Conjugate

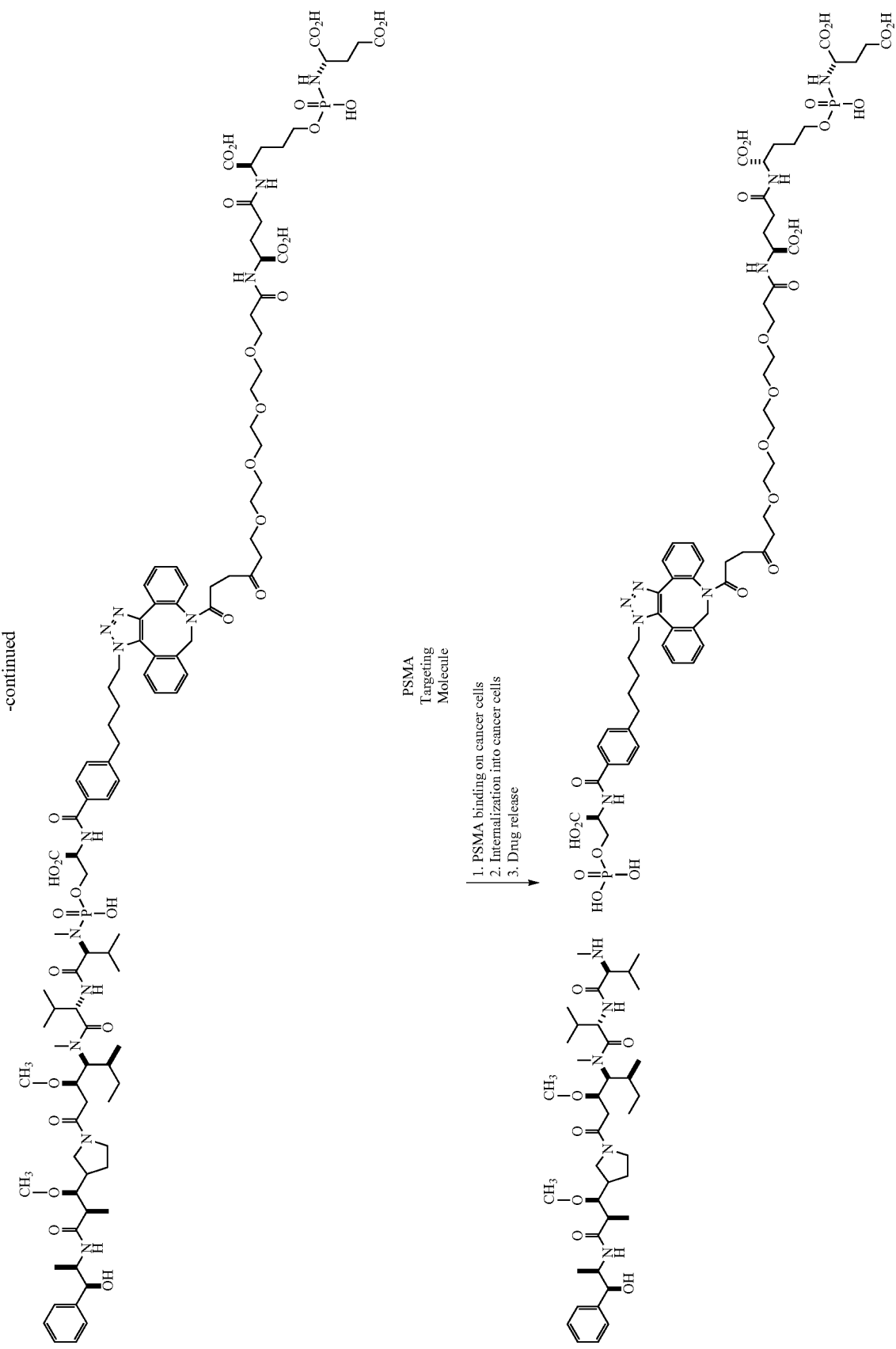

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The invention claimed is:

1. A conjugate or a salt thereof having formula (I)

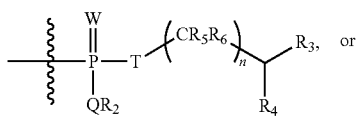  formula (I), wherein,
X is a therapeutic or diagnostic agent comprising a moiety for attaching to L or directly to Y,
L is a spacer comprising a moiety for attaching to Y;
m is 0 or 1;
when m is 0,
  X comprises a moiety $NR_1$, S, or O for attaching to Y; and
  $R_1$ is H, acyl, formyl, aryl, heteroaryl, heterocycloalkyl, substituted or unsubstituted alkyl, substituted or unsubstituted cycloalkyl, substituted or unsubstituted aryl, substituted or unsubstituted heteroaryl, substituted or unsubstituted alkyl-aryl, substituted or unsubstituted cycloalkyl-aryl, substituted or unsubstituted alkyl-heteroaryl, or substituted or unsubstituted cycloalkyl-heteroaryl;
when m is 1,
  X comprises $NR_1$, S or O for attaching to L;
  L comprises a moiety $NR_1$, S, or O for attaching to Y; and
  $R_1$ is H, acyl, formyl, aryl, heteroaryl, heterocycloalkyl, substituted or unsubstituted alkyl, substituted or unsubstituted cycloalkyl, substituted or unsubstituted aryl, substituted or unsubstituted heteroaryl, substituted or unsubstituted alkyl-aryl, substituted or unsubstituted cycloalkyl-aryl, substituted or unsubstituted alkyl-heteroaryl, or substituted or unsubstituted cycloalkyl-heteroaryl;
Y is a hydrolysable linker having formula (II) or formula (III)

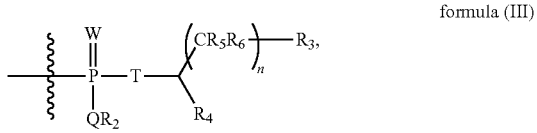

wherein,
W is O, S, or Se;
Q is N, O, S, or Se;
$R_2$ is H, substituted or unsubstituted alkyl, substituted or unsubstituted cycloalkyl, substituted or unsubstituted aryl, substituted or unsubstituted heteroaryl, substituted or unsubstituted alkyl-aryl, substituted or unsubstituted cycloalkyl-aryl, substituted or unsubstituted alkyl-heteroaryl, or substituted or unsubstituted cycloalkyl-heteroaryl;
$R_3$ is an ionizable group;
$R_4$ is H, lower alkyl, aryl, or a substituent comprising a functional group for attachment to a molecule;
$R_5$ and $R_6$ are independently, H, lower alkylene or arylene;
T is O, S, alkylene, arylene, acyl, formyl, or substituted or unsubstituted alkylarylene; and
n is 0, 1, 2, 3, 4, 5, 6, 7, 8, or 9.

2. The conjugate of claim 1 or a salt thereof, wherein the ionizable group is selected from the group consisting of a carboxylic acid; an ester of a carboxylic acid; a sulfonic acid; an ester of a sulfonic acid; a phosphoric acid; an ester of a phosphoric acid; a phosphonic acid; an ester of a phosphonic acid; a substituted or unsubstituted aromatic ring containing one or more carboxylic acids, esters of carboxylic acids, sulfonic acids, esters of a sulfonic acids, phosphoric acids, esters of a phosphoric acids, phosphonic acids, and esters of a phosphonic acids, a substituted or unsubstituted heterocyclic aromatic group containing one or more nitrogen atoms; a substituted or unsubstituted fused heterocyclic aromatic group containing one or more nitrogen atoms and containing one or more aromatic or aliphatic rings; a substituted or unsubstituted aniline group; and a substituted or unsubstituted fused aniline group containing one or more nitrogen atoms and containing one or more aromatic or aliphatic rings.

3. The conjugate of claim 1 or a salt thereof, wherein the therapeutic agent is selected from the group consisting an anti-angiogenic agent, a cytotoxic agent, a cytokine, a chemokine, an apoptotic agent, a prodrug, a toxin, an enzyme, a radioisotope, an immunomodulator, an antibiotic, an agent active in the CNS and a hormone.

4. The conjugate of claim 3 or a salt thereof, wherein the therapeutic agent contains an amine group.

5. The conjugate of claim 4 or a salt thereof, wherein the therapeutic agent is monomethylauristatin E (MMAE), monomethylauristatin F (MMAF), and doxorubicin.

6. The conjugate of claim 1 or a salt thereof, wherein the diagnostic agent is selected from the group consisting of a radioisotope, an imaging agent, a fluorescent dye, a near-IR dye, an enzyme, a chemiluminescent agent, a bioluminescent agent, a paramagnetic ion, an ultrasound label, and a radioacoustic label.

7. The conjugate of claim 1 or a salt thereof, wherein L comprises a self-immolating spacer, wherein the self-immolating spacer is a peptide or a protein.

8. The conjugate of claim 1 or a salt thereof, wherein $R_4$ is a substituent comprising a chemical or biorthogonal functional group for covalent attachment to a molecule.

9. The conjugate of claim 8 or a salt thereof, wherein the substituent comprises an azide, an alkyne, a maleimide, an iodoacetamide, a thiol, a disulfide, a NHS ester, a tetrazine, a trans-cyclooctene, a ketone/aldehyde, a hydrazine, a hydrazide, or a thioacid.

10. The conjugate of claim 8 or a salt thereof, wherein the conjugate further comprises a molecule attached through the functional group of $R_4$, wherein the molecule is a targeting molecule, a polymer, a solid support, an attachment handle, or masking agent.

11. The conjugate of claim 1 or a salt thereof, wherein
X is an agent comprising the substituent $NR_1$;
$R_1$ is H or alkyl;
T is O;
W is O;
Q is O;
$R_2$ is H;

R$_3$ is an ionizable group selected from the group consisting of is a carboxylic acid, an ester of a carboxylic acid, and a substituted or unsubstituted heterocyclic aromatic group containing one or more nitrogen atoms; and R$_4$ is a substituent comprising a functional group for attachment to a molecule.

12. The conjugate of claim 11 or a salt thereof, wherein R$_4$ is a substituent selected from the group consisting of an azide, an alkyne, a maleimide, an iodoacetamide, a thiol, a disulfide, a NHS ester, a tetrazine, a trans-cyclooctene, a ketone/aldehyde, a hydrazine, a hydrazide, and a thioacid.

13. The conjugate of claim 12 or a salt thereof, wherein the conjugate or a salt thereof further comprises a molecule and wherein the molecule is a targeting molecule attached through the substituent.

14. The conjugate of claim 13 or a salt thereof, wherein the targeting molecule is selected from the group consisting of a ligand, a substrate, a protein, a peptide, an aptamer, a carbohydrate, or a small molecule.

15. The conjugate of claim 13 or a salt thereof, wherein the targeting molecule targets tumors.

16. The conjugate of claim 15 or a salt thereof, wherein the targeting molecule targets prostate specific membrane antigen.

17. A composition comprising the conjugate of claim 1 or a salt thereof and a carrier.

18. A pharmaceutical composition comprising the conjugate of claim 1 or a salt thereof and a pharmaceutically acceptable carrier.

19. A method of delivering a therapeutic agent to a subject, wherein the method comprises administering a therapeutically effective amount of the pharmaceutical composition of claim 18 to a subject in need of such therapeutic agent, wherein X is a therapeutic agent.

20. The method of claim 19, wherein the conjugate or a salt thereof further comprises a targeting molecule attached through the substituent of R$_4$.

21. A method of treating cancer, wherein the method comprises administering a therapeutically effective amount of the pharmaceutical composition of claim 18 to a subject in need of such treatment, wherein X is a therapeutic agent and wherein the conjugate or a salt thereof further comprises a targeting molecule attached through the substituent of R$_4$.

22. A method of diagnosing cancer, wherein the method comprises
(a) administering an effective amount of the pharmaceutical composition of claim 18 to a subject in need of such diagnosis, wherein is X a diagnostic agent and wherein the conjugate or a salt thereof further comprises a targeting molecule attached through the functional group of R$_4$; and
(b) detecting the diagnostic agent.

23. The method of claim 21, wherein the targeting molecule targets a prostate specific membrane antigen on the tumor.

24. The conjugate of claim 1, wherein R$_4$ is H, lower alkyl, or aryl; and wherein R$_3$ is attached to a molecule.

25. The conjugate of claim 24, wherein the molecule is a targeting molecule, a detectable label, a polymer, or a solid support.

26. The conjugate of claim 24, wherein the molecule is attached to R$_3$ through a spacer.

27. The conjugate of claim 24, wherein R$_3$ further comprises a functional group for attaching to the molecule.

28. The conjugate of claim 10 or a salt thereof, wherein the targeting molecule, the polymer, the solid support, the attachment handle, or the masking agent is attached to the functional group of R$_4$ through a spacer.

29. The conjugate of claim 28 or a salt thereof, wherein the functional group of R$_4$ comprises an amide group or an amino group.

* * * * *